US011802145B2

(12) United States Patent
Kang et al.

(10) Patent No.: US 11,802,145 B2
(45) Date of Patent: Oct. 31, 2023

(54) RECOMBINANT PROTEIN TARGETING PD-1 AND TGFß

(71) Applicant: Nanjing Leads Biolabs Co., Ltd., Jiangsu (CN)

(72) Inventors: Xiaoqiang Kang, Plainsboro, NJ (US); Xiao Huang, Jiangsu (CN)

(73) Assignee: Nanjing Leads Biolabs Co., Ltd., Nanjing (CN)

(*) Notice: Subject to any disclaimer, the term of this patent is extended or adjusted under 35 U.S.C. 154(b) by 365 days.

(21) Appl. No.: 17/075,212

(22) Filed: Oct. 20, 2020

(65) Prior Publication Data

US 2021/0115142 A1    Apr. 22, 2021

Related U.S. Application Data

(60) Provisional application No. 62/924,154, filed on Oct. 21, 2019.

(51) Int. Cl.
| | |
|---|---|
| C07K 14/705 | (2006.01) |
| C07K 16/28 | (2006.01) |
| C07K 14/71 | (2006.01) |
| A61P 35/00 | (2006.01) |
| C12N 5/10 | (2006.01) |
| C12N 15/63 | (2006.01) |
| A61K 31/713 | (2006.01) |
| A61K 39/00 | (2006.01) |

(52) U.S. Cl.
CPC ...... *C07K 14/70596* (2013.01); *A61K 31/713* (2013.01); *A61P 35/00* (2018.01); *C07K 14/71* (2013.01); *C07K 16/2818* (2013.01); *C12N 5/10* (2013.01); *C12N 15/63* (2013.01); *A61K 2039/505* (2013.01); *C07K 2317/56* (2013.01); *C07K 2317/565* (2013.01); *C07K 2317/76* (2013.01); *C07K 2317/92* (2013.01); *C07K 2317/94* (2013.01); *C07K 2319/32* (2013.01); *C07K 2319/33* (2013.01)

(58) Field of Classification Search
CPC ............................ C07K 14/71; C07K 2319/32; C07K 2319/33; C07K 16/28; C12N 5/10; C12N 15/63
See application file for complete search history.

(56) References Cited

U.S. PATENT DOCUMENTS

| | | |
|---|---|---|
| 9,850,306 B2 | 12/2017 | Bedi et al. |
| 10,316,076 B2 | 6/2019 | Kumar et al. |
| 10,851,157 B2 | 12/2020 | Karow et al. |
| 2019/0352402 A1 | 11/2019 | Kang et al. |

FOREIGN PATENT DOCUMENTS

| | | |
|---|---|---|
| JP | 2017-506217 A | 3/2017 |
| JP | 2020-519289 A | 7/2020 |
| WO | WO 2015/027082 A1 | 2/2015 |
| WO | WO 2016/161410 A2 | 10/2016 |
| WO | WO 2017/037634 A1 | 3/2017 |
| WO | WO 2018/029367 A1 | 2/2018 |
| WO | WO 2020/006509 A1 | 1/2020 |
| WO | WO 2020/014285 A2 | 1/2020 |
| WO | WO 2020/094122 A1 | 5/2020 |

OTHER PUBLICATIONS

Chen et al. Fusion protein linkers: Property, design and functionality. Adv. Drug Del. Rev. 65, 1357-1369, 2013. (Year: 2013).*
PCT/CN2020/122242, mailed Jan. 21, 2021, International Search Report and Written Opinion.
International Search Report and Written Opinion dated Jan. 21, 2021 in connection with PCT/CN2020/122242. 12 pages.
Knudson et al., M7824, a novel bifunctional anti-PD-L1/TGFβ Trap fusion protein, promotes anti-tumor efficacy as monotherapy and in combination with vaccine. Oncoimmunology. Feb. 14, 2018;7(5):e1426519. Erratum in: Oncoimmunology. Feb. 27, 2019;8(5):e1584435. 15 pages total.
Ravi et al., Bifunctional immune checkpoint-targeted antibodyligand traps that simultaneously disable TGFβ enhance the efficacy of cancer immunotherapy. Nature Communications. Feb. 2018;9:741. 14 pages.

* cited by examiner

*Primary Examiner* — Elly-Gerald Stoica
(74) *Attorney, Agent, or Firm* — Wolf, Greenfield & Sacks, P.C.

(57) ABSTRACT

A recombinant fusion protein comprising 1) TGFβR2, or a fragment thereof, capable of binding to TGFβ, and 2) an antibody, or an antigen-binding fragment thereof, that binds to PD-1. Also disclosed are a polynucleotide encoding the recombinant fusion protein, an expression vector containing the polynucleotide, a method for producing the recombinant protein and a method for treating a disease caused by over expression of TGFβ and/or PD-1 using the recombinant protein.

17 Claims, 4 Drawing Sheets

Specification includes a Sequence Listing.

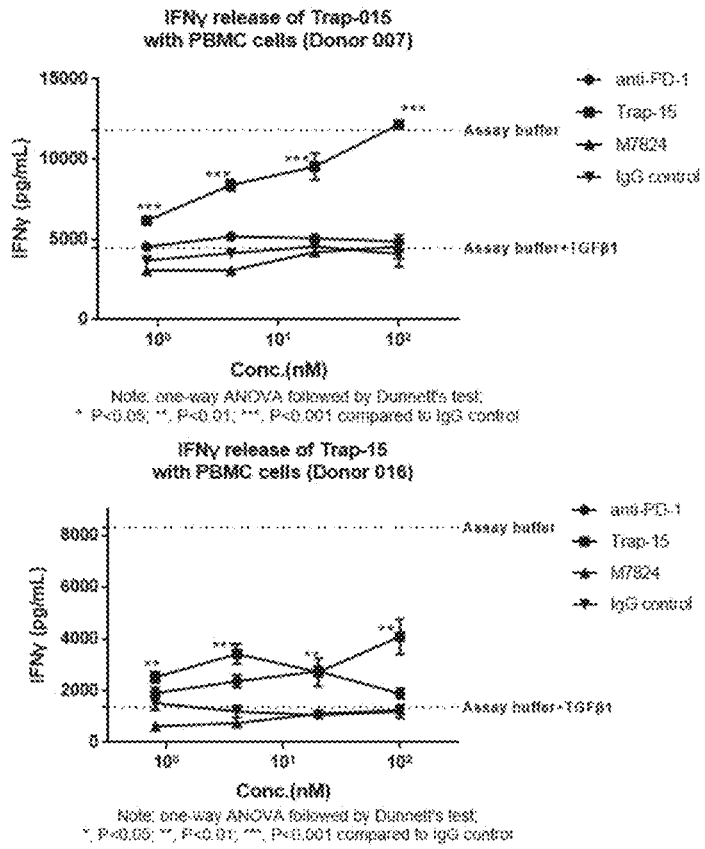
Fig.6 Trap-15 stimulated human PBMC to release IFNγ from donor 007 and donor 016
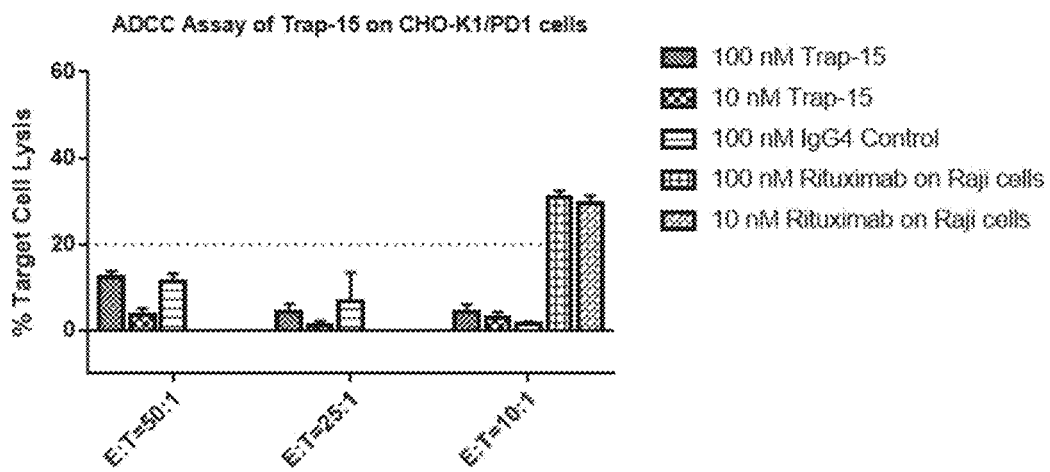
Fig.7 Trap-15 did not induce ADCC effect

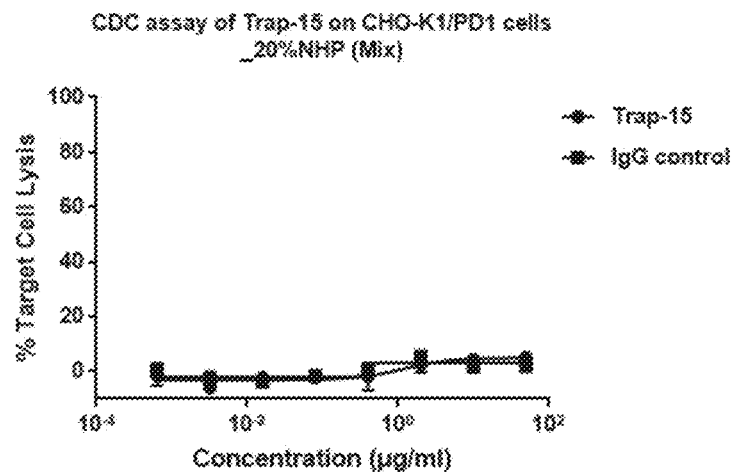
Fig. 8 Trap-15 did not induce CDC effect
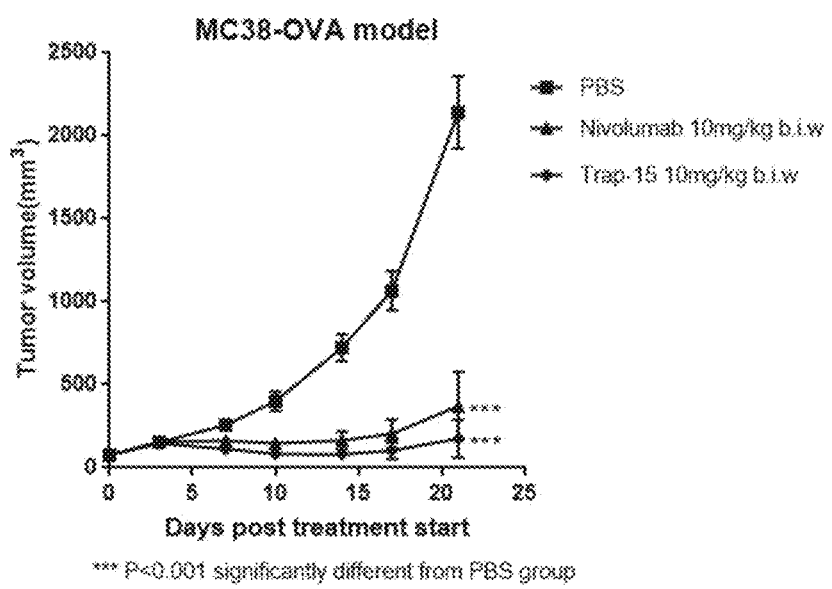
Fig 9. Tumor growth curve

SEQUENCE LISTING

```
<160> NUMBER OF SEQ ID NOS: 25

<210> SEQ ID NO 1
<211> LENGTH: 136
<212> TYPE: PRT
<213> ORGANISM: Artificial
<220> FEATURE:
<223> OTHER INFORMATION: TGFBETAR2 extracellular domain

<400> SEQUENCE: 1

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
```

```
              65                  70                  75                  80
        Pro Lys Leu Pro Tyr His Asp Phe Ile Leu Glu Asp Ala Ala Ser Pro
                            85                  90                  95

Lys Cys Ile Met Lys Glu Lys Lys Pro Gly Glu Thr Phe Phe Met
                        100                 105                 110

Cys Ser Cys Ser Ser Asp Glu Cys Asn Asp Asn Ile Ile Phe Ser Glu
                        115                 120                 125

Glu Tyr Asn Thr Ser Asn Pro Asp
                    130                 135

<210> SEQ ID NO 2
<211> LENGTH: 126
<212> TYPE: PRT
<213> ORGANISM: Artificial
<220> FEATURE:
<223> OTHER INFORMATION: Anti-PD-1 antibody Heavy chain variable region

<400> SEQUENCE: 2

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Pro Phe Gln Ser Tyr
                20                  25                  30

Tyr Ile His Trp Val Arg Gln Ala Pro Gly Gln Gly Leu Glu Trp Val
            35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
                100                 105                 110

Met Asp Val Trp Gly Lys Gly Thr Leu Val Thr Val Ser Ser
            115                 120                 125

<210> SEQ ID NO 3
<211> LENGTH: 112
<212> TYPE: PRT
<213> ORGANISM: Artificial
<220> FEATURE:
<223> OTHER INFORMATION: Anti-PD-1 antibody Light chain variable region

<400> SEQUENCE: 3

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Gln Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
                100                 105                 110
```

<210> SEQ ID NO 4
<211> LENGTH: 456
<212> TYPE: PRT
<213> ORGANISM: Artificial
<220> FEATURE:
<223> OTHER INFORMATION: Anti-PD-1 antibody Heavy chain

<400> SEQUENCE: 4

```
Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Pro Phe Gln Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Ala Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Ala Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365
```

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly Ala
                450                 455

<210> SEQ ID NO 5
<211> LENGTH: 219
<212> TYPE: PRT
<213> ORGANISM: Artificial
<220> FEATURE:
<223> OTHER INFORMATION: Anti-PD-1 antibody Light chain

<400> SEQUENCE: 5

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Gln Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 6
<211> LENGTH: 11
<212> TYPE: PRT
<213> ORGANISM: Artificial
<220> FEATURE:
<223> OTHER INFORMATION: Linker

<400> SEQUENCE: 6

Ser Pro Ala Pro Glu Leu Leu Gly Gly Pro Ser
1               5                   10

<210> SEQ ID NO 7
<211> LENGTH: 19
<212> TYPE: PRT
<213> ORGANISM: Artificial
<220> FEATURE:
<223> OTHER INFORMATION: Linker

<400> SEQUENCE: 7

Asp Lys Thr His Thr Cys Pro Pro Cys Pro Ala Pro Glu Leu Leu Gly
1               5                   10                  15

Gly Pro Ser

<210> SEQ ID NO 8
<211> LENGTH: 14
<212> TYPE: PRT
<213> ORGANISM: Artificial
<220> FEATURE:
<223> OTHER INFORMATION: Linker

<400> SEQUENCE: 8

Ser Lys Tyr Gly Pro Pro Cys Pro Pro Cys Gly Gly Pro Ser
1               5                   10

<210> SEQ ID NO 9
<211> LENGTH: 20
<212> TYPE: PRT
<213> ORGANISM: Artificial
<220> FEATURE:
<223> OTHER INFORMATION: Linker

<400> SEQUENCE: 9

Gly Gly Gly Gly Ser Gly Gly Gly Ser Gly Gly Gly Gly Ser Gly
1               5                   10                  15

Gly Gly Gly Ser
            20

<210> SEQ ID NO 10
<211> LENGTH: 603
<212> TYPE: PRT
<213> ORGANISM: Artificial
<220> FEATURE:
<223> OTHER INFORMATION: Heavy chain-linker-TGFBETAR2 extracellular
      domain

<400> SEQUENCE: 10

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Pro Phe Gln Ser Tyr
                20                  25                  30

Tyr Ile His Trp Val Arg Gln Ala Pro Gly Gln Gly Leu Glu Trp Val
            35                  40                  45

Gly Val Ile Asn Pro Ser Gly Gly Ser Thr Thr Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Val Val Tyr Tyr Cys
                85                  90                  95

Ala Arg Gly Ser Tyr Ser Ser Gly Trp Asp Tyr Tyr Tyr Tyr Gly
            100                 105                 110

-continued

```
Met Asp Val Trp Gly Lys Gly Thr Leu Val Thr Val Ser Ser Ala Ser
            115                 120                 125
Thr Lys Gly Pro Ser Val Phe Pro Leu Ala Pro Ser Ser Lys Ser Thr
    130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
        195                 200                 205
Cys Asn Val Asn His Lys Pro Ser Asn Thr Lys Val Asp Lys Lys Val
    210                 215                 220
Glu Pro Lys Ser Cys Asp Lys Thr His Thr Cys Pro Pro Cys Pro Ala
225                 230                 235                 240
Pro Glu Ala Ala Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Ala Val Ser His Glu Asp Pro Glu Val Lys Phe Asn Trp Tyr Val
        275                 280                 285
Asp Gly Val Glu Val His Asn Ala Lys Thr Lys Pro Arg Glu Glu Gln
    290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Ala Ala Pro Ile Glu Lys Thr Ile Ser Lys Ala Lys Gly Gln Pro
            340                 345                 350
Arg Glu Pro Gln Val Tyr Thr Leu Pro Pro Ser Arg Asp Glu Leu Thr
        355                 360                 365
Lys Asn Gln Val Ser Leu Thr Cys Leu Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
        435                 440                 445
Ser Leu Ser Leu Ser Pro Gly Ala Ser Pro Ala Pro Glu Leu Leu Gly
    450                 455                 460
Gly Pro Ser Ile Pro Pro His Val Gln Lys Ser Val Asn Asn Asp Met
465                 470                 475                 480
Ile Val Thr Asp Asn Asn Gly Ala Val Lys Phe Pro Gln Leu Cys Lys
                485                 490                 495
Phe Cys Asp Val Arg Phe Ser Thr Cys Asp Asn Gln Lys Ser Cys Met
            500                 505                 510
Ser Asn Cys Ser Ile Thr Ser Ile Cys Glu Lys Pro Gln Glu Val Cys
        515                 520                 525
```

```
Val Ala Val Trp Arg Lys Asn Asp Glu Asn Ile Thr Leu Glu Thr Val
        530                 535                 540

Cys His Asp Pro Lys Leu Pro Tyr His Asp Phe Ile Leu Glu Asp Ala
545                 550                 555                 560

Ala Ser Pro Lys Cys Ile Met Lys Glu Lys Lys Pro Gly Glu Thr
                565                 570                 575

Phe Phe Met Cys Ser Cys Ser Ser Asp Glu Cys Asn Asp Asn Ile Ile
            580                 585                 590

Phe Ser Glu Glu Tyr Asn Thr Ser Asn Pro Asp
        595                 600

<210> SEQ ID NO 11
<211> LENGTH: 611
<212> TYPE: PRT
<213> ORGANISM: Artificial
<220> FEATURE:
<223> OTHER INFORMATION: Heavy chain-linker-TGFBETAR2 extracellular
      domain

<400> SEQUENCE: 11

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Pro Phe Gln Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Ala Val Ser His Glu Asp Pro Glu Val Lys Phe Asn Trp Tyr Val
        275                 280                 285
```

Asp Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Ala Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Ala Asp Lys Thr His Thr Cys Pro Pro
450                 455                 460

Cys Pro Ala Pro Glu Leu Leu Gly Gly Pro Ser Ile Pro Pro His Val
465                 470                 475                 480

Gln Lys Ser Val Asn Asn Asp Met Ile Val Thr Asp Asn Asn Gly Ala
                485                 490                 495

Val Lys Phe Pro Gln Leu Cys Lys Phe Cys Asp Val Arg Phe Ser Thr
            500                 505                 510

Cys Asp Asn Gln Lys Ser Cys Met Ser Asn Cys Ser Ile Thr Ser Ile
        515                 520                 525

Cys Glu Lys Pro Gln Glu Val Cys Val Ala Val Trp Arg Lys Asn Asp
530                 535                 540

Glu Asn Ile Thr Leu Glu Thr Val Cys His Asp Pro Lys Leu Pro Tyr
545                 550                 555                 560

His Asp Phe Ile Leu Glu Asp Ala Ala Ser Pro Lys Cys Ile Met Lys
                565                 570                 575

Glu Lys Lys Lys Pro Gly Glu Thr Phe Phe Met Cys Ser Cys Ser Ser
            580                 585                 590

Asp Glu Cys Asn Asp Asn Ile Ile Phe Ser Glu Glu Tyr Asn Thr Ser
        595                 600                 605

Asn Pro Asp
    610

<210> SEQ ID NO 12
<211> LENGTH: 606
<212> TYPE: PRT
<213> ORGANISM: Artificial
<220> FEATURE:
<223> OTHER INFORMATION: Heavy chain-linker-TGFBETAR2 extracellular
      domain

<400> SEQUENCE: 12

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Pro Phe Gln Ser Tyr

```
                20                  25                  30
Tyr Ile His Trp Val Arg Gln Ala Pro Gly Gln Gly Leu Glu Trp Val
                35                  40                  45
Gly Val Ile Asn Pro Ser Gly Gly Ser Thr Thr Tyr Ala Gln Lys Phe
 50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Val Val Tyr Tyr Cys
                85                  90                  95
Ala Arg Gly Ser Tyr Ser Ser Gly Trp Asp Tyr Tyr Tyr Tyr Tyr Gly
                100                 105                 110
Met Asp Val Trp Gly Lys Gly Thr Leu Val Thr Val Ser Ser Ala Ser
                115                 120                 125
Thr Lys Gly Pro Ser Val Phe Pro Leu Ala Pro Ser Ser Lys Ser Thr
            130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
            195                 200                 205
Cys Asn Val Asn His Lys Pro Ser Asn Thr Lys Val Asp Lys Lys Val
        210                 215                 220
Glu Pro Lys Ser Cys Asp Lys Thr His Thr Cys Pro Pro Cys Pro Ala
225                 230                 235                 240
Pro Glu Ala Ala Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Ala Val Ser His Glu Asp Pro Glu Val Lys Phe Asn Trp Tyr Val
        275                 280                 285
Asp Gly Val Glu Val His Asn Ala Lys Thr Lys Pro Arg Glu Glu Gln
    290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Ala Ala Pro Ile Glu Lys Thr Ile Ser Lys Ala Lys Gly Gln Pro
            340                 345                 350
Arg Glu Pro Gln Val Tyr Thr Leu Pro Pro Ser Arg Asp Glu Leu Thr
        355                 360                 365
Lys Asn Gln Val Ser Leu Thr Cys Leu Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
        435                 440                 445
```

Ser Leu Ser Leu Ser Pro Gly Ala Ser Lys Tyr Gly Pro Cys Pro
    450                 455                 460

Pro Cys Gly Gly Pro Ser Ile Pro Pro His Val Gln Lys Ser Val Asn
465                 470                 475                 480

Asn Asp Met Ile Val Thr Asp Asn Asn Gly Ala Val Lys Phe Pro Gln
                485                 490                 495

Leu Cys Lys Phe Cys Asp Val Arg Phe Ser Thr Cys Asp Asn Gln Lys
            500                 505                 510

Ser Cys Met Ser Asn Cys Ser Ile Thr Ser Ile Cys Glu Lys Pro Gln
        515                 520                 525

Glu Val Cys Val Ala Val Trp Arg Lys Asn Asp Glu Asn Ile Thr Leu
    530                 535                 540

Glu Thr Val Cys His Asp Pro Lys Leu Pro Tyr His Asp Phe Ile Leu
545                 550                 555                 560

Glu Asp Ala Ala Ser Pro Lys Cys Ile Met Lys Glu Lys Lys Lys Pro
                565                 570                 575

Gly Glu Thr Phe Phe Met Cys Ser Cys Ser Ser Asp Glu Cys Asn Asp
            580                 585                 590

Asn Ile Ile Phe Ser Glu Glu Tyr Asn Thr Ser Asn Pro Asp
        595                 600                 605

<210> SEQ ID NO 13
<211> LENGTH: 612
<212> TYPE: PRT
<213> ORGANISM: Artificial
<220> FEATURE:
<223> OTHER INFORMATION: Heavy chain-linker-TGFBETAR2 extracellular
      domain

<400> SEQUENCE: 13

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Pro Phe Gln Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile

```
                195                 200                 205
Cys Asn Val Asn His Lys Pro Ser Asn Thr Lys Val Asp Lys Lys Val
210                 215                 220
Glu Pro Lys Ser Cys Asp Lys Thr His Thr Cys Pro Pro Cys Pro Ala
225                 230                 235                 240
Pro Glu Ala Ala Gly Gly Pro Ser Val Phe Leu Phe Pro Pro Lys Pro
                    245                 250                 255
Lys Asp Thr Leu Met Ile Ser Arg Thr Pro Glu Val Thr Cys Val Val
                260                 265                 270
Val Ala Val Ser His Glu Asp Pro Glu Val Lys Phe Asn Trp Tyr Val
                275                 280                 285
Asp Gly Val Glu Val His Asn Ala Lys Thr Lys Pro Arg Glu Glu Gln
290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                    325                 330                 335
Leu Ala Ala Pro Ile Glu Lys Thr Ile Ser Lys Ala Lys Gly Gln Pro
                340                 345                 350
Arg Glu Pro Gln Val Tyr Thr Leu Pro Pro Ser Arg Asp Glu Leu Thr
                355                 360                 365
Lys Asn Gln Val Ser Leu Thr Cys Leu Val Lys Gly Phe Tyr Pro Ser
370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                    405                 410                 415
Ser Lys Leu Thr Val Asp Lys Ser Arg Trp Gln Gln Gly Asn Val Phe
                420                 425                 430
Ser Cys Ser Val Met His Glu Ala Leu His Asn His Tyr Thr Gln Lys
                435                 440                 445
Ser Leu Ser Leu Ser Pro Gly Ala Gly Gly Gly Ser Gly Gly Gly
450                 455                 460
Gly Ser Gly Gly Gly Ser Gly Gly Gly Ser Ile Pro Pro His
465                 470                 475                 480
Val Gln Lys Ser Val Asn Asn Asp Met Ile Val Thr Asp Asn Asn Gly
                    485                 490                 495
Ala Val Lys Phe Pro Gln Leu Cys Lys Phe Cys Asp Val Arg Phe Ser
                500                 505                 510
Thr Cys Asp Asn Gln Lys Ser Cys Met Ser Asn Cys Ser Ile Thr Ser
                515                 520                 525
Ile Cys Glu Lys Pro Gln Glu Val Cys Val Ala Val Trp Arg Lys Asn
                530                 535                 540
Asp Glu Asn Ile Thr Leu Glu Thr Val Cys His Asp Pro Lys Leu Pro
545                 550                 555                 560
Tyr His Asp Phe Ile Leu Glu Asp Ala Ala Ser Pro Lys Cys Ile Met
                    565                 570                 575
Lys Glu Lys Lys Lys Pro Gly Glu Thr Phe Phe Met Cys Ser Cys Ser
                580                 585                 590
Ser Asp Glu Cys Asn Asp Asn Ile Ile Phe Ser Glu Glu Tyr Asn Thr
                595                 600                 605
Ser Asn Pro Asp
610
```

<210> SEQ ID NO 14
<211> LENGTH: 456
<212> TYPE: PRT
<213> ORGANISM: Artificial
<220> FEATURE:
<223> OTHER INFORMATION: Positive control- anti-PD-1 antibody 21F12-1F6 Heavy chain

<400> SEQUENCE: 14

```
Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Gln Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Ala Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Ala Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
```

```
              355                 360                 365
Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
450                 455
```

<210> SEQ ID NO 15
<211> LENGTH: 607
<212> TYPE: PRT
<213> ORGANISM: Artificial
<220> FEATURE:
<223> OTHER INFORMATION: Anti-PD-L1 antibody M7824 Heavy chain

<400> SEQUENCE: 15

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

```
                    260                 265                 270
Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Ala Gly Gly Gly Ser Gly Gly Gly Ser Gly Gly Gly Gly
    450                 455                 460

Ser Gly Gly Gly Ser Gly Ile Pro Pro His Val Gln Lys Ser Val
465                 470                 475                 480

Asn Asn Asp Met Ile Val Thr Asp Asn Asn Gly Ala Val Lys Phe Pro
                485                 490                 495

Gln Leu Cys Lys Phe Cys Asp Val Arg Phe Ser Thr Cys Asp Asn Gln
            500                 505                 510

Lys Ser Cys Met Ser Asn Cys Ser Ile Thr Ser Ile Cys Glu Lys Pro
        515                 520                 525

Gln Glu Val Cys Val Ala Val Trp Arg Lys Asn Asp Glu Asn Ile Thr
    530                 535                 540

Leu Glu Thr Val Cys His Asp Pro Lys Leu Pro Tyr His Asp Phe Ile
545                 550                 555                 560

Leu Glu Asp Ala Ala Ser Pro Lys Cys Ile Met Lys Glu Lys Lys
                565                 570                 575

Pro Gly Glu Thr Phe Phe Met Cys Ser Cys Ser Ser Asp Glu Cys Asn
            580                 585                 590

Asp Asn Ile Ile Phe Ser Glu Glu Tyr Asn Thr Ser Asn Pro Asp
        595                 600                 605

<210> SEQ ID NO 16
<211> LENGTH: 216
<212> TYPE: PRT
<213> ORGANISM: Artificial
<220> FEATURE:
<223> OTHER INFORMATION: Anti-PD-L1 antibody M7824 Light chain

<400> SEQUENCE: 16

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
```

-continued

```
                    20                  25                  30
Asn Tyr Val Ser Trp Tyr Gln Gln His Pro Gly Lys Ala Pro Lys Leu
                35                  40                  45
Met Ile Tyr Asp Val Ser Asn Arg Pro Ser Gly Val Ser Asn Arg Phe
 50                  55                  60
Ser Gly Ser Lys Ser Gly Asn Thr Ala Ser Leu Thr Ile Ser Gly Leu
 65                  70                  75                  80
Gln Ala Glu Asp Glu Ala Asp Tyr Tyr Cys Ser Ser Tyr Thr Ser Ser
                85                  90                  95
Ser Thr Arg Val Phe Gly Thr Gly Thr Lys Val Thr Val Leu Gly Gln
                100                 105                 110
Pro Lys Ala Asn Pro Thr Val Thr Leu Phe Pro Pro Ser Ser Glu Glu
                115                 120                 125
Leu Gln Ala Asn Lys Ala Thr Leu Val Cys Leu Ile Ser Asp Phe Tyr
                130                 135                 140
Pro Gly Ala Val Thr Val Ala Trp Lys Ala Asp Gly Ser Pro Val Lys
145                 150                 155                 160
Ala Gly Val Glu Thr Thr Lys Pro Ser Lys Gln Ser Asn Asn Lys Tyr
                165                 170                 175
Ala Ala Ser Ser Tyr Leu Ser Leu Thr Pro Glu Gln Trp Lys Ser His
                180                 185                 190
Arg Ser Tyr Ser Cys Gln Val Thr His Glu Gly Ser Thr Val Glu Lys
                195                 200                 205
Thr Val Ala Pro Thr Glu Cys Ser
                210                 215
```

<210> SEQ ID NO 17
<211> LENGTH: 290
<212> TYPE: PRT
<213> ORGANISM: Artificial
<220> FEATURE:
<223> OTHER INFORMATION: Human PD-L1

<400> SEQUENCE: 17

```
Met Arg Ile Phe Ala Val Phe Ile Phe Met Thr Tyr Trp His Leu Leu
 1               5                  10                  15
Asn Ala Phe Thr Val Thr Val Pro Lys Asp Leu Tyr Val Val Glu Tyr
                20                  25                  30
Gly Ser Asn Met Thr Ile Glu Cys Lys Phe Pro Val Glu Lys Gln Leu
                35                  40                  45
Asp Leu Ala Ala Leu Ile Val Tyr Trp Glu Met Glu Asp Lys Asn Ile
 50                  55                  60
Ile Gln Phe Val His Gly Glu Glu Asp Leu Lys Val Gln His Ser Ser
 65                  70                  75                  80
Tyr Arg Gln Arg Ala Arg Leu Leu Lys Asp Gln Leu Ser Leu Gly Asn
                85                  90                  95
Ala Ala Leu Gln Ile Thr Asp Val Lys Leu Gln Asp Ala Gly Val Tyr
                100                 105                 110
Arg Cys Met Ile Ser Tyr Gly Gly Ala Asp Tyr Lys Arg Ile Thr Val
                115                 120                 125
Lys Val Asn Ala Pro Tyr Asn Lys Ile Asn Gln Arg Ile Leu Val Val
                130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
```

```
                    165                 170                 175
Gly Lys Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290

<210> SEQ ID NO 18
<211> LENGTH: 367
<212> TYPE: PRT
<213> ORGANISM: Artificial
<220> FEATURE:
<223> OTHER INFORMATION: OKT3-scFv

<400> SEQUENCE: 18

Met Glu Arg His Trp Ile Phe Leu Leu Leu Ser Val Thr Ala Gly
1               5                   10                  15

Val His Ser Gln Val Gln Leu Gln Gln Ser Gly Ala Glu Leu Ala Arg
                20                  25                  30

Pro Gly Ala Ser Val Lys Met Ser Cys Lys Ala Ser Gly Tyr Thr Phe
            35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65              70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Gly Gly Gly Gly Ser Gly
        130                 135                 140

Gly Gly Gly Ser Gly Gly Gly Ser Gln Ile Val Leu Thr Gln Ser
145                 150                 155                 160

Pro Ala Ile Met Ser Ala Ser Pro Gly Glu Lys Val Thr Met Thr Cys
                165                 170                 175

Ser Ala Ser Ser Ser Val Ser Tyr Met Asn Trp Tyr Gln Gln Lys Ser
            180                 185                 190

Gly Thr Ser Pro Lys Arg Trp Ile Tyr Asp Thr Ser Lys Leu Ala Ser
        195                 200                 205

Gly Val Pro Ala His Phe Arg Gly Ser Gly Ser Gly Thr Ser Tyr Ser
        210                 215                 220

Leu Thr Ile Ser Gly Met Glu Ala Glu Asp Ala Ala Thr Tyr Tyr Cys
```

```
                225                 230                 235                 240
Gln Gln Trp Ser Ser Asn Pro Phe Thr Phe Gly Ser Gly Thr Lys Leu
                245                 250                 255

Glu Ile Asn Ser Ser Val Val Pro Val Leu Gln Lys Val Asn Ser Thr
                260                 265                 270

Thr Thr Lys Pro Val Leu Arg Thr Pro Ser Pro Val His Pro Thr Gly
                275                 280                 285

Thr Ser Gln Pro Gln Arg Pro Glu Asp Cys Arg Pro Arg Gly Ser Val
            290                 295                 300

Lys Gly Thr Gly Leu Asp Phe Ala Cys Asp Ile Tyr Ile Trp Ala Pro
305                 310                 315                 320

Leu Ala Gly Ile Cys Val Ala Leu Leu Leu Ser Leu Ile Ile Thr Leu
                325                 330                 335

Ile Cys Tyr His Arg Ser Arg Lys Arg Val Cys Lys Cys Pro Arg Pro
                340                 345                 350

Leu Val Arg Gln Glu Gly Lys Pro Arg Pro Ser Glu Lys Ile Val
                355                 360                 365

<210> SEQ ID NO 19
<211> LENGTH: 288
<212> TYPE: PRT
<213> ORGANISM: Artificial
<220> FEATURE:
<223> OTHER INFORMATION: Human PD-1

<400> SEQUENCE: 19

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
```

```
                 225                 230                 235                 240
Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 20
<211> LENGTH: 440
<212> TYPE: PRT
<213> ORGANISM: Artificial
<220> FEATURE:
<223> OTHER INFORMATION: Heavy chain for Nivolumab

<400> SEQUENCE: 20

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
                100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
                180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
        210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
                260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
        290                 295                 300

Asp Trp Leu Asn Gly Lys Glu Tyr Lys Cys Lys Val Ser Asn Lys Gly
```

```
                        305                 310                 315                 320
Leu Pro Ser Ser Ile Glu Lys Thr Ile Ser Lys Ala Lys Gly Gln Pro
                    325                 330                 335

Arg Glu Pro Gln Val Tyr Thr Leu Pro Pro Ser Gln Glu Glu Met Thr
                340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 21
<211> LENGTH: 214
<212> TYPE: PRT
<213> ORGANISM: Artificial
<220> FEATURE:
<223> OTHER INFORMATION: Light chain for Nivolumab

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 22
<211> LENGTH: 446
<212> TYPE: PRT
<213> ORGANISM: Artificial
<220> FEATURE:
<223> OTHER INFORMATION: Heavy chain of IgG Control

<400> SEQUENCE: 22

Gln Val Gln Leu Val Glu Ser Gly Gly Gly Ala Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Leu Tyr Asp Gly Ser Asp Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Val Ala Gly Thr His Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
```

```
                    370                 375                 380
Gln Pro Glu Asn Asn Tyr Lys Thr Thr Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 23
<211> LENGTH: 214
<212> TYPE: PRT
<213> ORGANISM: Artificial
<220> FEATURE:
<223> OTHER INFORMATION: Light chain of IgG Control

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 446
<212> TYPE: PRT
<213> ORGANISM: Artificial
<220> FEATURE:
<223> OTHER INFORMATION: IgG4 control heavy chain

<400> SEQUENCE: 24

Gln Val Gln Leu Val Glu Ser Gly Gly Gly Ala Val Gln Pro Gly Arg
1               5                   10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Leu Tyr Asp Gly Ser Asp Lys Phe Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Val Ala Gly Thr His Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
```

```
                     435                 440                 445

<210> SEQ ID NO 25
<211> LENGTH: 214
<212> TYPE: PRT
<213> ORGANISM: Artificial
<220> FEATURE:
<223> OTHER INFORMATION: IgG4 control Light chain

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

RECOMBINANT PROTEIN TARGETING PD-1 AND TGFß

CROSS REFERENCE TO RELATED APPLICATION

The present application claims the benefit of U.S. Provisional Application Ser. No. 62/924,154, filed on Oct. 21, 2019. The aforementioned application is hereby incorporated by reference herein.

FIELD OF THE INVENTION

The present disclosure relates to a recombinant fusion protein targeting PD-1 and TGFβ, and the preparation and use thereof.

BACKGROUND OF THE INVENTION

According to the World Health Organization, cancer is the second leading cause of death globally, and an estimated 9.6 million people died of cancer in 2018.

Cancer is actually a group of diseases involving abnormal cell growth and division. The cancer cells are quite "smart" and have developed several mechanisms to evade a host's immune surveillance. For example, they express a high level of membrane proteins PD-L1 and PD-L2, which two bind to PD-1 on the surface of T cells and induce T cell exhaustion (Oscar Arrieta et al., (2017) *Oncotarget* 8(60): 101994-102005). The cancer cells also increase transforming growth factor β (TGFβ) expression, most commonly TGFβ1, to inhibit cell killing by cytotoxic lymphocytes and NK cells, by decreasing the expression of the activating immune-receptor NKG2D in CD8+ T cells and NK cells and repressing the expression of the NKG2D ligand MICA (Masato Morikawa et al., (2016) *Cold Spring Harb Perspect Biol* 8: a021873; Joan Massague (2008) *Cell* 134(2): 215-230; Paul Spear et al., (2013) *Cancer Immun.* 13:8.

Efforts have been made on early diagnosis and proper treatment of cancer, and the overall mortality related to cancer is decreasing. The current options for cancer treatment include surgery, radiation therapy, chemotherapy, hormone therapy, targeted therapy, immunotherapy, and so on. Among these, immunotherapy is a type of treatment that helps the immune system fight cancer by amplifying immune responses. Immunotherapy is not yet widely used as surgery, chemotherapy and radiation therapy, but have achieved considerable success in recent years. Pharmaceuticals targeting the immune-suppressive pathways such as antibodies are used in the immunotherapy.

PD-1

PD-1, also known as CD279, is a cell surface receptor. It has two ligands, PD-L1 and PD-L2. PD-L1 expression is upregulated on macrophages and dendritic cells in response to LPS and GM-CSF treatment, and on T cells and B cells upon TCR and B cell receptor signaling, and PD-L1 mRNA is detected in mice heart, lung, thymus, spleen and kidney (Freeman G J et al., (2000) Journal of Experimental Medicine 192(7):1027; Yamazaki T et al., (2002) Journal of Immunology 169(10):5538-5545). PD-L1 is also expressed on tumor cells. PD-L2 has a more restricted expression profile.

When bound with PD-L1 or PD-L2, PD-1 down-regulates the immune system and promotes self-tolerance by suppressing T cell inflammatory activity. The inhibitory effect of PD-1 on immune system may prevent autoimmune diseases. On the other hand, increased local PD-L1 expression in cancer cells may prevent the immune system from killing these cells. Several anti-PD-1 antibodies, such as Opdivo® (BMS) and Keytruda® (Merck), have been proved for clinical cancer treatment, alone or in combination with other anti-tumor agents.

TGFβ

Transforming growth factor beta (TGFβ) is a bi-functional cytokine that has three mammalian isoforms, TGFβ1, TGFβ2 and TGFβ3. TGFβ complexes with other factors to form a serine/threonine kinase complex that binds to TGFβ receptors and activates downstream substrates and regulatory proteins. The TGFβ signaling mostly conveys strong growth inhibitory activity in most cell types. For example, TGFβ inhibits proliferation of T-lymphocytes and thymocytes. TGFβ also stimulates proliferation of some cells under certain conditions. For example, TGFβ, in combination with IL-2, induces Treg cell differentiation. Cancer cells express a high level of TGFβ1 to suppress the immune function, and at the same time disables the tumor-suppressive action of TGFβ by mutational inactivation of core pathway components or losing the tumor-suppressive arm of the signaling pathway.

The TGFβ receptors, TGFβR1 and TGFβR2, both have a high affinity for TGFβ1. TGFβR2 is a transmembrane protein consisting of a C-terminal protein kinase domain and an N-terminal ectodomain. The ectodomain consists of a compact fold containing nine beta-strands and a single helix stabilized by a network of six intra-strand disulfide bonds. T cell-specific expression of TGFβR2 may prevent the growth of inoculated melanoma or thymoma in mice.

Therapy Targeting More than One Molecules

Pharmaceuticals targeting a single tumor-associated antigen or a single immune-suppressive pathway are sometimes found to have limited therapeutic efficacy. For example, the anti-VEGF antibody Avastin® is proved to inhibit cancer cell growth to certain extent, but cannot eliminate the cancer cells. In addition, the overall response rate of an approved anti-PD-L1 antibody, Avelumab (BAVENCIO), is only 33%.

Therefore, in clinical trials and clinical treatments, a pharmaceutical agent is usually administered in combination with another therapeutic agent, such that the target cells, such as cancer cells, are attacked in several ways. Alternatively, a single molecule drug having two or more target binding specificities, such as a bispecific or multi-specific antibody/protein, may be developed to enable a therapy targeting more than one molecules. For example, EMD Serono have developed a bispecific fusion protein, M7824, containing an anti-PD-L1 antibody linked to the extracellular domain of TGFβR2 for treatment of multiple solid cancers, including non-small cell lung and biliary tract cancers.

SUMMARY OF THE INVENTION

The present disclosure discloses a recombinant fusion protein, comprising 1) TGFβR2, or a fragment thereof, capable of binding to TGFβ, and 2) an antibody, or an antigen-binding fragment thereof, that binds to PD-1. The recombinant fusion protein captures TGFβ in a tumor microenvironment to reduce the inhibitory effect on immune cell proliferation and function, and also blocks the interaction of PD-L1 on tumor cells with PD-1 on immune cells to release the check on immune cells by PD-1-mediated inhibitory signals. By targeting two immune-suppressive pathways, the recombinant fusion protein of the disclosure enhances immune response to tumor cells.

TGFβR2 of the present disclosure may be human TGFβR2. The TGFβR2 fragment of the present disclosure may be a TGFβR2 extracellular domain. In some embodiments, the recombinant fusion protein of the present disclosure comprises a TGFβR2 extracellular domain comprising an amino acid sequence having 85%, 86%, 87%, 88%, 89%, 90%, 91%, 92%, 93%, 94%, 95%, 96%, 970, 98%, 99% or 100% identity to SEQ ID NO: 1, wherein the TGFβR2 extracellular domain binds to TGFβ.

The antibody binding to PD-1 of the present disclosure may be a human or humanized anti-PD-1 antibody. In some embodiments, the antibody binding to PD-1 of the present disclosure comprises a heavy chain variable region having an amino acid sequence having 85%, 86%, 87%, 88%, 89%, 90%, 91%, 92%, 93%, 94%, 95%, 96%, 97%, 98%, 99% or 100% identity to SEQ ID NO: 2 and a light chain variable region having an amino acid sequence having 85%, 86%, 87%, 88%, 89%, 90%, 91%, 92%, 93%, 94%, 95%, 96%, 97%, 98%, 99% or 100% identity to SEQ ID NO: 3, optionally with a human IgG1, IgG4 heavy chain constant region and a human kappa light chain constant region, wherein the antibody binds to PD-1 and blocks PD-1-PD-L1 interaction. In one embodiment, the antibody binding to PD-1 comprises a heavy chain having an amino acid sequence having 85%, 86%, 87%, 88%, 89%, 90%, 91%, 92%, 93%, 94%, 95%, 96%, 97%, 98%, 99% or 100% identity to SEQ ID NO: 4, and a light chain having an amino acid sequence having 85%, 86%, 87%, 88%, 89%, 90%, 91%, 92%, 93%, 94%, 95%, 96%, 97%, 98%, 99% or 100% identity to SEQ ID NO: 5, wherein the antibody binds to PD-1 and blocks PD-1-PD-L1 interaction. The antigen-binding fragment may be an scFv, Fab, F(ab')$_2$ or Fv fragment.

The TGFβR2 or a fragment thereof may be linked via a linker to the antibody or an antigen-binding fragment thereof. The linker may be a peptide of about 5 to 30 amino acid residues. In an embodiment, the linker is a peptide of 10 to 30 amino acid residues. In another embodiment, the linker is a peptide of 10 to 20 amino acid residues. The linker may be one having an amino acid sequence set forth in SEQ ID NOs.: 6, 7, 8 or 9.

The recombinant fusion protein of the present disclosure may comprises a TGFβR2 fragment linked to an anti-PD-1 antibody at the N- or C-terminus of a heavy or light chain.

The recombinant fusion protein of the present disclosure may comprise a TGFβR2 extracellular domain linked via a linker to an anti-PD-1 antibody at the C-terminus of the heavy chain constant region. In some embodiments, the TGFβR2 extracellular domain comprises an amino acid sequence of SEQ ID NO: 1. The anti-PD-1 antibody comprises a heavy chain of SEQ ID NO: 4 and a light chain variable region of SEQ ID NO: 5. The linker comprises an amino acid sequence set forth in SEQ ID NOs.: 6, 7, 8 or 9. The anti-PD-1 heavy chain-linker-TGFβR2 extracellular domain comprises an amino acid sequence of SEQ ID NOs.: 10, 11, 12 or 13.

The recombinant fusion protein of the disclosure remains the binding capacity to both TGFβ and PD-1, and shows superior PD-L1-PD-1 blocking activities and other pharmaceutical properties as compared to prior art bispecific fusion protein M7824.

In one embodiment, the present application provides a recombinant fusion protein, comprising:
 a) a human TGFβR2 fragment, and
 b) an antibody comprising a heavy chain and a light chain, wherein the human TGFβR2 fragment is linked to the C-terminus of the heavy chain.

In one embodiment, the present application provides a recombinant fusion protein, comprising:
 a) a human TGFβR2 fragment, and
 b) a (Fab')$_2$ comprising a heavy chain variable region and a light chain variable region,
 wherein the TGFβR2 fragment is linked to the C-terminus of the heavy chain variable region.

In one embodiment, the present application provides a recombinant fusion protein comprising an anti-PD-1 antibody or an antigen binding fragment thereof and a human TGFβR2 fragment, wherein the anti-PD-1 antibody or an antigen binding fragment thereof comprises 6CDRs of a heavy chain variable region of SEQ ID NO:2 and a light chain variable region of SEQ ID NO:3.

In one embodiment, the present application provides a recombinant fusion protein, wherein the TGFβR2 extracellular domain comprises an amino acid sequence of SEQ ID NO: 1, or an amino acid sequence having at least 90% identity with SEQ ID NO: 1

In one embodiment, the present application provides a recombinant fusion protein, wherein the antibody or the antigen-binding fragment thereof comprises a heavy chain variable region comprising an amino acid sequence of SEQ ID NO: 2 or an amino acid sequence having at least 90% identity with SEQ ID NO: 2 and simultaneously having 3CDRs of SEQ ID NO: 2, and a light chain variable region comprising an amino acid sequence of SEQ ID NO: 3 or an amino acid sequence having at least 90% identity with SEQ ID NO:3 and simultaneously having 3CDRs of SEQ ID NO:3.

In one embodiment, the present application provides a recombinant fusion protein, wherein the heavy chain comprises an amino acid sequence of SEQ ID NO: 4 or an amino acid sequence having at least 80% identity with SEQ ID NO: 4 and simultaneously having 3CDRs of SEQ ID NO: 4, and the light chain comprises an amino acid sequence of SEQ ID NO: 5 or an amino acid sequence having at least 80% identity with SEQ ID NO:5 and simultaneously having 3CDRs of SEQ ID NO:5.

In one embodiment, the present application provides a recombinant fusion protein comprising two peptides, wherein the first peptide comprises a heavy chain of a human anti-PD-1 antibody, a linker and a TGFβRII extracellular domain, and the second peptide comprises a light chain of the human anti-PD-1 antibody.

In one embodiment, the present application provides a recombinant fusion protein, selected from:
 1) a recombinant fusion protein comprising an amino acid sequence of SEQ ID NO: 10 or an amino acid sequence having at least 80% identity with SEQ ID NO:10 and simultaneously having 3CDRs of SEQ ID NO:4; and an amino acid sequence of SEQ ID NO: 5 or an amino acid sequence having at least 80% identity with SEQ ID NO:5 and simultaneously having 3CDRs of SEQ ID NO:5:
 2) a recombinant fusion protein comprising an amino acid sequence of SEQ ID NO: 11 or an amino acid sequence having at least 80% identity with SEQ ID NO:11 and simultaneously having 3CDRs of SEQ ID NO: 4, and an amino acid sequence of SEQ ID NO: 5 or an amino acid sequence having at least 80% identity with SEQ ID NO:5 and simultaneously having 3CDRs of SEQ ID NO:5;
 3) a recombinant fusion protein comprising an amino acid sequence of SEQ ID NO: 12 or an amino acid sequence having at least 80% identity with SEQ ID NO:12 and simultaneously having 3CDRs of SEQ ID NO:4, and an amino acid sequence of SEQ ID NO: 5 or an amino acid sequence having at least 80% identity with SEQ ID NO:5 and simultaneously having 3CDRs of SEQ ID NO:5; or 4) a recombinant fusion protein comprising an amino acid sequence of SEQ ID NO: 13 or an amino acid sequence having at least 80% identity with SEQ ID NO:13 and simultaneously having 3CDRs of SEQ ID NO: 4, and an amino acid sequence of SEQ ID NO: 5 or an amino acid sequence having at least 80% identity with SEQ ID NO:5 and simultaneously having 3CDRs of SEQ ID NO:5.

In a further embodiment, the present application provides a recombinant fusion protein comprising two peptides, wherein the first peptide comprises an amino acid sequence as shown in SEQ ID NO:10 and the second peptide comprises an amino acid sequence as shown in SEQ ID NO:5. Preferably, the first peptide consists of an amino acid sequence as shown in SEQ ID NO:10 and the second peptide consists of an amino acid as shown in SEQ ID NO:5.

In a further embodiment, the present application provides a recombinant fusion protein comprising two peptides, wherein the first peptide comprises an amino acid sequence as shown in SEQ ID NO:11 and the second peptide comprises an amino acid sequence as shown in SEQ ID NO:5. Preferably, the first peptide consists of an amino acid sequence as shown in SEQ ID NO:11 and the second peptide consists of an amino acid as shown in SEQ ID NO:5.

In a further embodiment, the present application provides a recombinant fusion protein comprising two peptides, wherein the first peptide comprises an amino acid sequence as shown in SEQ ID NO:12 and the second peptide comprises an amino acid sequence as shown in SEQ ID NO:5. Preferably, the first peptide consists of an amino acid sequence as shown in SEQ ID NO:12 and the second peptide consists of an amino acid as shown in SEQ ID NO:5.

In a further embodiment, the present application provides a recombinant fusion protein comprising two peptides, wherein the first peptide comprises an amino acid sequence as shown in SEQ ID NO:13 and the second peptide comprises an amino acid sequence as shown in SEQ ID NO5. Preferably, the first peptide consists of an amino acid sequence as shown in SEQ ID NO:13 and the second peptide consists of an amino acid as shown in SEQ ID NO:5.

In one aspect, a nucleic acid molecule encoding the recombinant fusion protein of the present invention is also provided, as well as an expression vector comprising the nucleic acid and a host cell comprising the expression vector.

In another aspect, a method for preparing the recombinant fusion protein using the host cell comprising the expression vector is also provided, and comprises steps of (i) expressing the recombinant fusion protein in the host cell and (ii) isolating the recombinant fusion protein from the host cell.

In another respect, the present invention provides a pharmaceutical composition, comprising the recombinant fusion protein of the present invention, and at least one pharmaceutically acceptable carrier. The pharmaceutical composition may further comprise at least one adjuvant.

In another aspect, the present invention provides a method for treating a disease caused by over-expression of TGFβ and/or PD-L1, comprising administering to a patient or a subject in need thereof a therapeutically effective amount of the recombinant fusion protein of the present invention or the pharmaceutical composition of the present invention.

In another aspect, the present invention provides the use of the recombinant fusion protein in the manufacture of a pharmaceutical composition for the treatment of a disease caused by over-expression of TGFβ and/or PD-L1.

In one embodiment, the method of the present invention is for inhibiting cancer/tumor growth. The cancer or tumor may be selected from the group consisting of colorectal, breast, ovarian, pancreatic, gastric, prostate, renal, cervical, myeloma, lymphoma, leukemia, thyroid, endometrial, uterine, bladder, neuroendocrine, head and neck, liver, nasopharyngeal, testicular, small cell lung cancer, non-small cell lung cancer, melanoma, basal cell skin cancer, squamous cell skin cancer, dermatofibrosarcoma protuberans, Merkel cell carcinoma, glioblastoma, glioma, sarcoma, mesothelioma, and myelodisplastic syndromes.

Other features and advantages of the instant disclosure will be apparent from the following detailed description and examples, which should not be construed as limiting. The contents of all references, Genbank entries, patents and published patent applications cited throughout this application are expressly incorporated herein by reference.

DESCRIPTION OF THE DRAWINGS

FIG. 6 shows Trap-15 can stimulate human PBMC to release IFNγ.

FIG. 7 shows Trap-15 does not induce ADCC effect.

FIG. 8 shows Trap-15 does not induce CDC effect.

FIG. 9. shows Trap-15 can significantly inhibit tumor growth.

DETAILED DESCRIPTION OF THE INVENTION

Figure 1:
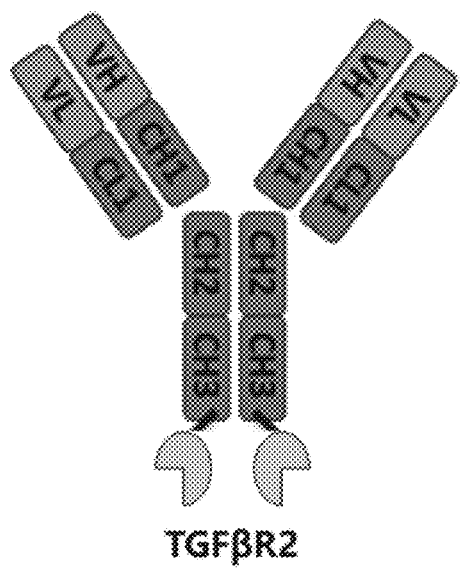
FIG. 1 is a schematic diagram of the structure of an exemplary recombinant fusion protein of the disclosure.

There are principally three different approaches to targeting two or more pharmacologies of tumor growth. Most commonly, patients can be given a cocktail of two or more different drugs. Although this option allows for maximal flexibility with respect to possible drug combinations and different dosages, it suffers from (a) potentially poor adherence to treatment by the patient because of the increased pill burden and the different dosing schedules for the individual drugs, (b) possible incompatibilities because of drug-drug interactions, and (c) increased risk of drug side effects. These problems can reduce the effectiveness of therapy and hamper the attainment of treatment goals particularly in the management of chronic diseases such as cancer.

The second approach relies on the use of fixed-dose combinations of drugs in a single dosage form. This approach reduces pill burden, resulting in improved patient compliance. The disadvantage of fixed-dose combinations is primarily the limited choice of possible dose ratios between the active ingredients, which makes it more difficult to properly titrate the individual patient to maximum efficacy with minimal adverse effects. In addition, different pharmacokinetic properties of the components in the combination might lead to a complex temporal mismatch in pharmacodynamic effects at the individual targets thereby compromising overall efficacy.

The third approach is the use of multifunctional drugs that combine two or more pharmacologies in a single compound. The design and validation of such multifunctional molecules are more complex and require substantial investigation into the optimal ratio of target activities in the molecule, but the unified pharmacokinetics may yield matched pharmacodynamic activities at the molecular targets. Multifunctional molecules may also be amenable to fixed dose combination with other drugs thereby combining three or even four pharmacologies in a single pill to produce further increments in efficacy.

The present inventors have invented a novel recombinant multi-functional fusion protein, which comprises TGFβRII or a TGFβRII fragment that binds to TGFβ and an antibody or an antigen binding portion thereof that binds to PD-1. The recombinant fusion protein captures TGFβ in the tumor microenvironment and thus reduces TGFβ's inhibitory effect on immune cell proliferation and function, and further blocks PD-L1-PD-1 interaction to release the check on immune cells by PD-1-mediated inhibitory signals, enhancing cancer cell killings by immune cells.

As used herein, the use of the word "a" or "an" when used in conjunction with the term "comprising" in the claims and/or the specification can mean "one," but it is also consistent with the meaning of "one or more," "at least one" and "one or more than one."

The terms "comprise(s)," "include(s)," "having," "has," "can," "contain(s)" and variants thereof, as used herein, are intended to be open-ended transitional phrases, terms or words that do not preclude the possibility of additional acts or structures. The present disclosure also contemplates other embodiments "comprising," "consisting of" and "consisting essentially of," the embodiments or elements presented herein, whether explicitly set forth or not.

The term "about" or "approximately" means within an acceptable error range for the particular value as determined by one of ordinary skill in the art, which will depend in part on how the value is measured or determined, i.e., the limitations of the measurement system. Alternatively, "about" can mean a range of up to 20%, preferably up to 10%, more preferably up to 5%, and more preferably still up to 1% of a given value.

The term "TGFβRII" or "TGFβ Receptor II" refers to a polypeptide having the wild-type human TGFβ Receptor Type 2 Isoform A sequence (e.g., the amino acid sequence of NCBI Reference Sequence (RefSeq) Accession No. NP_001020018), or a polypeptide having the wild-type human TGFβ Receptor Type 2 Isoform B sequence (e.g., the amino acid sequence of NCBI RefSeq Accession No. NP_003233). The TGFβRII may retain at least 0.1%, 0.5%, 1%, 5%, 10%, 25%, 35%, 50%, 75%, 90%, 95%, or 99% of the TGFβ-binding activity of the wild-type sequence. By a "fragment of TGFβRII capable of binding TGFβ" is meant any portion of NCBI RefSeq Accession No. NP_001020018 or of NCBI RefSeq Accession No. NP_003233 that retains the TGFβ-binding activity.

The term "antibody" as referred to herein includes whole antibodies and any antigen binding fragment (i.e., "antigen-binding portion") or single chains thereof. Whole antibodies are glycoproteins comprising two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody or "antigen-binding fragment" of an antibody can be used interchangeably throughout the present application and can be simply referred as "antibody portion" or "antibody fragment", respectively. Term "antigen-binding portion", as used herein, refers to one or more fragments of an antibody that retain the ability to specifically bind to an antigen (e.g., a PD-1 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "fusion protein" is used herein in the broadest sense and comprises one or more than one peptide. Examples of "fusion protein" is, but not limited to an immunoconjugate. An "immunoconjugate" is an antibody conjugated to one or more heterologous molecule(s), including but not limited to a cytokine. In an embodiment, the fusion protein of the present is an immunoconjugate comprising an anti-PD-1 antibody and a TGFβRII.

The two main components contained in the fusion protein of the present disclosure are the TGFβRII or TGFβRII fragment, and the anti-PD-1 antibody or antigen binding portion thereof. A person of ordinary skills in the art will recognize that there are many design choices for selecting the above two components. Preferably, human-derived sequence is used in human cancer therapies, as the strong immunogenicity of the proteins or peptides from non-human animals may lead to allergy and other adverse effects. However, other animal proteins or peptides, humanized if appropriate, may also be used in the present invention based on different application purposes.

TGFβRII may be human TGFβRII, and a TGFβRII extracellular domain may be preferred to construct the fusion protein in a relatively smaller size. The TGFβRII extracellular domain may have an amino acid sequence of SEQ ID NO: 1.

The anti-PD-1 antibody in the fusion protein of the disclosure is described in PCT/CN2019/087287 in detail where the heavy chain constant region is modified to eliminate the antibody dependent cell-mediated cytotoxicity (ADCC) and complement dependent cytotoxicity (CDC).

In the present disclosure, the TGFβRII extracellular domain is linked to the C-terminus of the heavy chain or heavy chain constant region in some embodiments, partly for the purpose of elimination of ADCC and CDC. In other embodiments, the TGFβRII extracellular domain may be linked to the N-terminus of the heavy chain or light chain (variable region), or alternatively the C-terminus of the light chain or light chain constant region. The antibody heavy chain constant region may be removed or modified to reduce ADCC and CDC, but removal of the heavy chain constant region may shorten the half-life of the fusion protein in human body.

A linker may be used when necessary between the TGFβRII extracellular domain and the anti-PD-1 antibody. Linkers serve primarily as a spacer. The linker may be made up of amino acids linked together by peptide bonds, preferably from 5 to 30 amino acids linked by peptide bonds, wherein the amino acids are selected from the 20 naturally occurring amino acids. One or more of these amino acids may be glycosylated, as is understood by those of skill in the art. In one embodiment, the 5 to 30 amino acids may be selected from glycine, alanine, proline, asparagine, glutamine, serine and lysine. In one embodiment, a linker is made up of a majority of amino acids that are sterically unhindered, such as glycine and alanine. Exemplary linkers are polyglycines (particularly (Glys, $(Gly)_8$, poly(Gly-Ala), and polyalanines. One exemplary suitable linker as shown in the Examples below is (Gly-Ser), such as -(Gly-Gly-Gly-Gly-Ser)$_3$-. Linkers may also be non-peptide linkers. For example, alkyl linkers such as —NH—, —$(CH_2)$s-C(O)—, wherein s=2-20 can be used. These alkyl linkers may further be substituted by any non-sterically hindering group such as lower alkyl (e.g., $C_{1-4}$) lower acyl, halogen (e.g., Cl, Br), CN, $NH_2$, phenyl, etc.

Also, the present invention provides a polynucleotide molecule encoding the recombinant fusion protein and an expression vector expressing the recombinant bi-functional fusion protein. Examples of vectors include but are not limited to plasmids, viral vectors, yeast artificial chromosomes (YACs), bacterial artificial chromosomes (BACs), transformation-competent artificial chromosomes (TACs), mammalian artificial chromosomes (MACs) and human artificial episomal chromosomes (HAECs).

The present invention provides host cells comprising the above expression vectors. The host cells may be transformed or transfected with the expression vectors. Suitable host cells include *Escherichia coli*, yeasts and other eukaryotes. Preferably. *Escherichia coli*, yeast or mammalian cell lines (such as COS or CHO) are used.

In another aspect, the present disclosure provides a pharmaceutical composition comprising the fusion protein of the present invention formulated together with a pharmaceutically acceptable adjuvant. The composition may optionally contain one or more additional pharmaceutically active ingredients, such as another antibody or a drug. The pharmaceutical compositions of the invention also can be administered in a combination therapy with, for example, another immune-stimulatory agent, anti-cancer agent, an anti-viral agent, or a vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: The Science and Practice of Pharmacy, 20th Ed. (Lippincott Williams & Wilkins 2003), the disclosure of which is incorporated herein by reference.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in injection. For example, the vehicle or carrier may be neutral buffered saline or saline mixed with serum albumin. Other exemplary pharmaceutical compositions comprise Tris buffers, or acetate buffers, which may further include sorbitol or a suitable substitute thereof. In one embodiment of the present invention, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose.

Preferably, the pharmaceutical composition is suitable for intravenous, intramuscular, subcutaneous, parenteral, spinal or epidermal administration (e.g., by injection or infusion). Depending on the route of administration, the active molecule can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, the fusion protein can be administered as a sustained release formulation, in which case less frequent administration is required.

For administration of the fusion protein, the dosage ranges from about 0.0001 to 100 mg/kg, and more usually 0.01 to 10 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration twice per week, once per week, once every two weeks, once every three weeks, once every four weeks, once a month, once every 3 months or once every three to 6 months. Preferred dosage regimens for the fusion protein of the invention include 3 mg/kg body weight or 6 mg/kg body weight via intraperitoneal administration, with the antibody being given using one of the following dosing schedules: (i) every four weeks for six dosages, then every three months; (ii) every three weeks; (iii) 3 mg/kg body weight once followed by 1 mg/kg body weight every three weeks; (vi) 6 mg/kg body weight, one dosage per week. In some methods, dosage is adjusted to achieve a plasma antibody concentration of about 1-1000 μg/ml and in some methods about 25-300 μg/ml.

A "therapeutically effective dosage" of a fusion protein of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 40%, more preferably by at least about 60%, even more preferably by at least about 80%, and still more preferably by at least about 99% relative to untreated subjects. A therapeutically effective amount of a fusion protein of the present invention can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312, 335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475, 196); the disclosures of which are incorporated herein by reference.

In certain embodiments, the fusion protein of the invention can be formulated to ensure proper distribution in vivo. For example, to ensure that the therapeutic fusion proteins of the invention cross the blood-brain barrier, they can be formulated in liposomes, which may additionally comprise targeting moieties to enhance selective transport to specific cells or organs. See, e.g. U.S. Pat. Nos. 4,522,811; 5,374, 548; 5,416,016; and 5,399,331.

A gene therapy in vivo is also envisioned wherein a nucleic acid molecule encoding the recombinant fusion protein of the present invention, or a derivative thereof is introduced directly into the subject. For example, a nucleic acid sequence encoding a recombinant fusion protein of the present invention is introduced into target cells via local injection of a nucleic acid construct with or without an appropriate delivery vector, such as an adeno-associated virus vector. Alternative viral vectors include, but are not limited to, retroviruses, adenovirus, herpes simplex vims and papilloma virus vectors. Physical transfer of the virus vector may be achieved in vivo by local injection of the desired nucleic acid construct or other appropriate delivery vector containing the desired nucleic acid sequence, liposome-mediated transfer, direct injection (naked DNA), or microparticle bombardment (gene-gun).

The compositions of the present disclosure may be used alone or in combination with other therapeutic agents to enhance their therapeutic effects or decrease potential side effects.

Another object of the present invention is to provide a method for preparing the above recombinant fusion protein and the pharmaceutical composition comprising the same. In one embodiment, the method comprises (1) providing an protein-encoding polynucleotide molecule; (2) constructing an expression vector comprising the polynucleotide molecule of (1); (3) transfecting or transforming suitable host cells with the expression vector of (2) and cultivating the host cells to express the protein; and (4) purifying the protein. The preparation may be carried out with well-known technologies by an ordinarily skilled artisan.

Another object of the present invention is to provide a method of treating cancer using the recombinant fusion protein of the present invention or the pharmaceutical composition of the present invention, comprising administrating an effective amount of the aforementioned pharmaceutical composition to the patients or subjects in need thereof. In one embodiment, the pharmaceutical composition is used to treat TGFβ and/or PD-L1-overexpressing tumors or cancers, including but not limited to colorectal, breast, ovarian, pancreatic, gastric, prostate, renal, cervical, myeloma, lymphoma, leukemia, thyroid, endometrial, uterine, bladder, neuroendocrine, head and neck, liver, nasopharyngeal, testicular, small cell lung cancer, non-small cell lung cancer, melanoma, basal cell skin cancer, squamous cell skin cancer, dermatofibrosarcoma protuberans, Merkel cell carcinoma, glioblastoma, glioma, sarcoma, mesothelioma, and myelodisplastic syndromes.

The present invention is now further described with the non-limiting examples below.

EXAMPLES

In the examples below, four exemplary fusion proteins of the disclosure, Trap-12, Trap-13, Trap-14 and Trap-15, were prepared and tested. A schematic drawing of the fusion proteins is shown in FIG. 1 comprising one anti-PD-1 antibody fused to two TGFβRII extracellular domains vis a linker.

Trap-12 was formed by two polypeptides of SEQ ID NO: 10 and two polypeptides of SEQ ID NO: 5. Trap-13 was formed by two polypeptides of SEQ ID NO: 11 and two polypeptides of SEQ ID NO: 5. Trap-14 contained two polypeptides of SEQ ID NO: 12 and two polypeptides of SEQ ID NO: 5. Trap-15 contained two polypeptides of SEQ ID NO: 13 and two polypeptides of SEQ ID NO: 5.

Example 1. Construction of Vectors Expressing Trap-12, Trap-13, Trap-14 and Trap-15

Nucleotide acids encoding the heavy chain-linker-TGFβRII extracellular domain (amino acids set forth in SEQ ID NOs.: 10, 11, 12 and 13, respectively) and the light chain (amino acid set forth in SEQ ID NO: 5) were synthesized by GENEWIZ and cloned into the expression vector pcDNA3.1 respectively.

Example 2. Protein Expression and Purification

The vectors constructed in Example 1 were co-transfected into CHO-S cells using ExpiCHO Expression System (ThermoFisher) according to manufacturer's instructions. Culture supernatants were harvested on Day 12 and purified with Protein A affinity chromatography (GE healthcare).

Example 3. Exemplary Fusion Proteins Bound to PD-1

An ELISA assay was performed for determination of the relative binding capacity of the fusion proteins to human PD-1.

Figure 2:
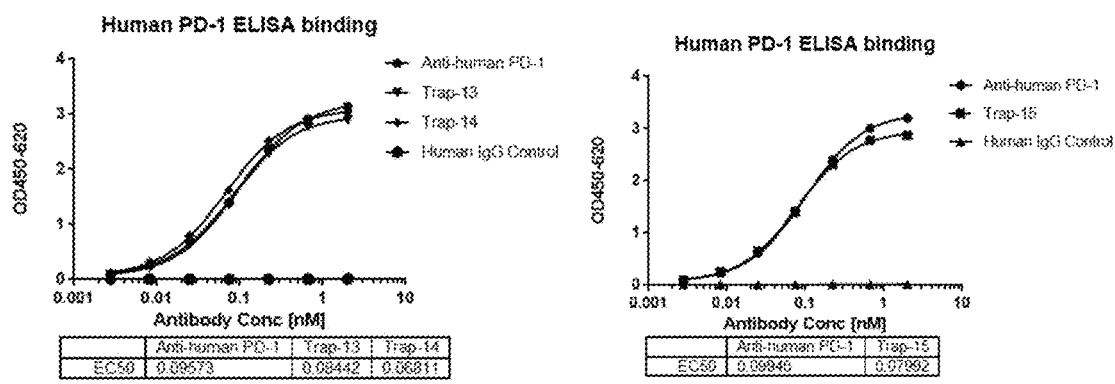
FIG. 2 shows the binding activities of the fusion proteins Trap-13, Trap-14 (left) and Trap-15 (right) to human PD-1.

Human PD-1 protein (ACRObiosystems, Cat #PD1-H5221) was immobilized onto 96-well plates in PBS (Hyclone, Cat #SH30256.01) by incubation overnight at 4° C., 25 ng/well. The plates were then blocked by incubation with 1% BSA in PBS for one hour at 37° C. After blocking, the plates were washed three times with PBST (PBS containing 0.05% Tween 20). Serially diluted fusion proteins (Trap-13, Trap-14 and Trap-15), an anti-PD-1 antibody as a positive control (antibody 21F12-1F6 in PCT/CN2019/087287, also referred to as anti-human PD-1 herein, with a heavy chain and a light chain having amino acid sequences of SEQ ID NOs.: 14 and 5, respectively) and an in house made anti-TIM3 antibody as a negative control (also referred to as human IgG control herein, antibody TIM3-6.12 disclosed in PCT/CN2019/082318) were prepared in binding buffer (PBS containing 0.05% Tween20 and 0.5% BSA) and incubated with the immobilized PD-1 proteins for one hour at 37° C. After binding, the plates were washed three times with PBST, incubated for one hour at 37° C. with peroxidase-labeled Goat anti-human F(ab')$^2$ antibody (Jackson Immuno Research, Cat #109-035-097) diluted 1/20,000 in binding buffer, washed again, developed with TMB (ThermoFisher, Cat #34028) for 15 minutes, and then stopped with 1M H$_2$SO$_4$. Each plate well contained 50 μL of solution at each step. The absorbance at 450 nm-620 nm was determined, and the EC$_{50}$ values and binding curves for the fusion protein binding to human PD-1 were shown in FIG. 2.

The data showed that the fusion proteins of the disclosure maintained the PD-1 binding capacities, had comparable EC$_{50}$ values with antibody 21F12-1F6.

Example 4. Exemplary Fusion Proteins Bound to TGFβ1

An ELISA assay was performed for determination of the relative binding capacity of the fusion proteins to human TGFβ1.

Figure 3:
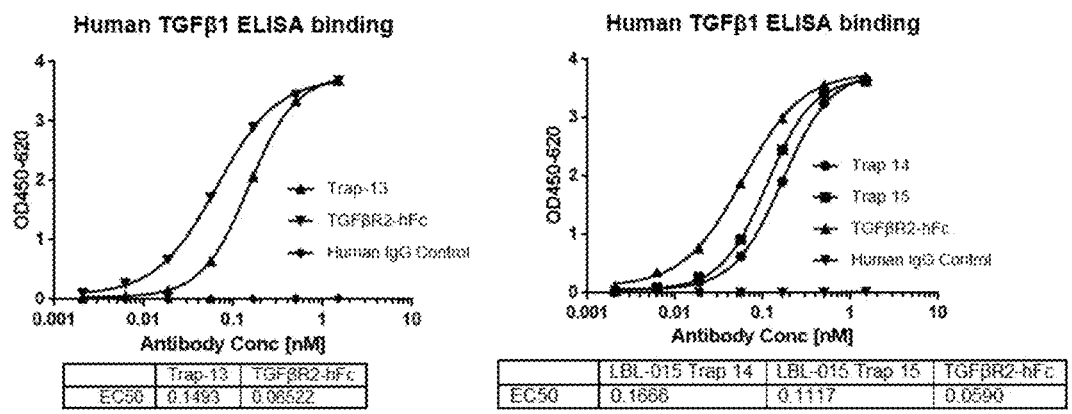
FIG. 3 shows the binding activities of the fusion proteins Trap-13 (left), Trap-14 and Trap-15 (right) to human TGFβ1.

Human TGFβ1 protein (Novoprotein Inc., Cat #CA59) was immobilized onto 96-well plates in PBS (Hyclone, Cat #SH30256.01) by incubation overnight at 4° C., 10 ng/well. The plates were then blocked by incubation with 1% BSA in PBS for one hour at 37° C. After blocking, the plates were washed three times with PBST (PBS containing 0.05% Tween 20). Serially diluted fusion proteins (Trap-13, Trap-14 and Trap-15), human TGFβR2-hFc as a positive control (ACRObiosystems, Cat #TG2-H5252) and an anti-TIM3 antibody as a negative control were prepared in binding buffer (PBS containing 0.05% Tween 20 and 0.5% BSA) and incubated with the immobilized Human TGFβ1 proteins for one hour at 37° C. After binding, the plates were washed three times with PBST, incubated for one hour at 37° C. with peroxidase-labeled Goat anti-human Fc antibody (Jackson Immuno Research, Cat #109-035-098) diluted 1/20,000 in binding buffer, washed again, developed with TMB (ThermoFisher Cat #34028) for 15 minutes, and then stopped with 1M H$_2$SO$_4$. The absorbance at 450 nm-620 nm was determined. The EC$_5$ values and binding curves for the fusion protein binding to human TGFβ1 were shown in FIG. 3.

The date suggested the fusion proteins of the disclosure bound to human TGFβ1, had similar EC$_{50}$ values with human TGFβR2-hFc.

Example 5. Exemplary Fusion Protein's Binding Affinities to PD-1 and TGFβ1

The kinetic binding activities of Trap-15 to human PD-1, cynomolgus PD-1, human TGFβ1 and rat TGFβ1 were measured by bio-layer interferometry (BLI) using a ForteBio Octet RED96.

AHC Biosensors (ForteBio, Cat #18-5060) were pre-soaked with Running Buffer (IX PBS Hyclone, Cat #SH30256.01, with 0.02% Tween20. pH7.0), dipped in Running Buffer for 100 seconds to establish a baseline, and then immersed in a well with Trap-15 at 5 μg/mL in Running Buffer until the Biosensors were loaded with 0.8 nM Trap-15. The biosensors were dipped in Running Buffer for 100 seconds for baseline balance. Then the biosensors were dipped in wells with serially diluted human PD-1 (Acrobiosystems, Cat #PD1-H5221) or cynomolgus PD-1 (Acrobiosystems, Cat. #PD1-C5223) at 400 nM, 200 nM, 100 nM, 50 nM, 25 nM, 12.5 nM, and 6.25 nM in Running Buffer for 200 seconds, and then immersed in Running Buffer for 600 seconds.

AHC Biosensors (ForteBio, Cat #18-5060) were pre-soaked with Running Buffer (IX PBS Hyclone, Cat #SH30256.01, with 0.02% Tween20. pH7.0), dipped in Running Buffer for 100 seconds to establish a baseline, and then immersed in a well with Trap-15 at 20 μg/mL in Running Buffer until the Biosensors were loaded with 1.2 nM Trap-15. The biosensors were dipped in Running Buffer for 100 seconds for baseline balance. Then the biosensors were dipped in wells with serially diluted human TGFβ1 (Sinobiological, Cat. 10804-HNAC) and rat TGFβ1 (Novoprotein, Cat. CK33) at 100 nM, 50 nM, 25 nM, 12.5 nM, 6.25 nM, 3.12 nM and 1.56 nM in Running Buffer for 60 seconds, and then immersed in Running Buffer for 600 seconds.

The association and dissociation curves were fit to a 1:1 Langmuir binding model using Octet evaluation software. The K$_a$, K$_d$ and K$_D$ values were determined and summarized in Table 1 below.

The data showed that Trap-15 bound to the four proteins with high affinities.

TABLE 1

Binding affinities of Trap-15 to PD-1 and TGFβ1

| Fusion protein | protein | $K_{on}(M^{-1}S^{-1})$ | $K_{off}(S^{-1})$ | $K_D(M)$ |
|---|---|---|---|---|
| Trap-15 | human PD-1 | 1.40E+05 | 7.36E-04 | 5.24E-09 |
| | cynomolgus PD-1 | 1.25E+05 | 1.20E-03 | 9.66E-09 |
| | human TGFβ1 | 1.40E+06 | 1.90E-04 | 1.36E-10 |
| | rat TGFβ1 | 1.36E+06 | 9.74E-05 | 7.19E-11 |

Example 6. Exemplary Fusion Protein Blocked TGFβ-TGFβR Interaction

TGFβ proteins bind to TGFβ receptors on the cell surface, initiating a signaling cascade that leads to phosphorylation and activation of SMAD2 and SMAD3, which then form a complex with SMAD4. The SMAD complex then translocate to the nucleus and binds to the SMAD binding element (SBE) in the nucleus, leading to transcription and expression of TGFβ/SMAD responsive genes. The activities of the fusion proteins of the disclosure on blocking TGFβ-TGFβR interaction were tested based on this.

A stable cell line 293T/SBE-luc2P was prepared by transfecting 293T cells with pGL4.48[luc2P/SBE/Hygro] (Promega, Cat #E367A) using Lipofectamine™ 2000 Reagent (Invitrogen, Cat #11668027) followed by limited dilution. The obtained cells were cultured in DMEM (Gibco, Cat #11995065) containing 10% FBS (Gibco, Cat #10099141) and 85 µg/mL Hygromycin B (Gibco, Cat #10687010).

293T/SBE-luc2P cells in DMEM with 10% FBS were loaded to a 96-well plate (Corning, Cat #3917), 50000 cells/well. Serially diluted Trap-15 and a control antibody (M7824, described in US 2015/0225483 A1, having a heavy chain-linker-TGFβR fragment of SEQ ID NO: 15 and a light chain of SEQ ID NO: 16) in DMEM having 10% FBS and 1.2 ng/ml TGFβ1 protein (Sino, 10804-HNAC) were respectively incubated at RT for about 30 min and then added at 60 µl/well to the 96-well plate containing the 293T/SBE-luc2P cells. The plate was incubated in a 37° C., 5% $CO_2$ incubator for 16-18 hours. Then, 60 µl/well of supernatant was discarded and 60 µl/well of One-Glo™ Reagent (Promega, Cat #E6130) was added to the assay plate. Luminescence was measured using a luminescence plate reader (Tecan, F200).

Figure 4:
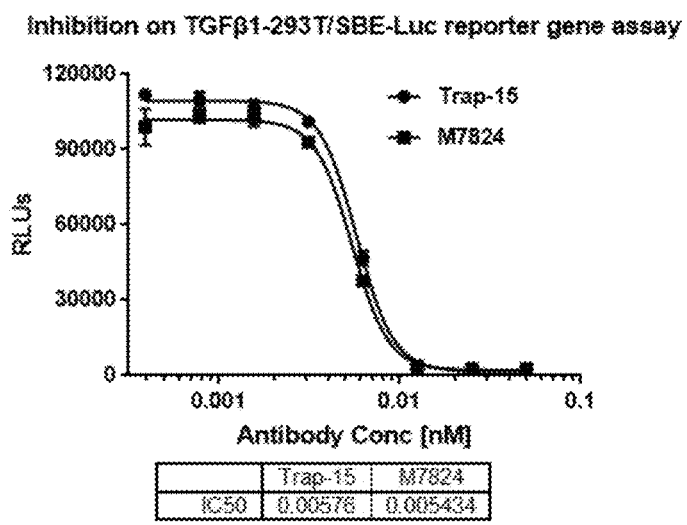
FIG. 4 shows the blocking activity of Trap-15 on TGFβ-TGFβR interaction.

$IC_{50}$ values were determined with the inhibitor dose-response variable slope (four parameters) fitted by GraphPad Prism, and the dose-dependent curve was shown in FIG. 4.

The result indicated that the blocking activity of Trap-15 was comparable with the M7824.

Example 7. Exemplary Fusion Protein Blocked PD-1-PD-L1 Interaction

When Jurkat-NFAT-PD-1 effector cells expressing PD-1 are co-cultured with CHO-OKT3-PD-L1 target cells expressing PD-L1, little TCR-NFAT mediated luminescence will be observed due to PD-1-PD-L1 interaction. Luminescence will be seen when the PD-1-PD-L1 interaction is blocked. Therefore, the activities of the fusion proteins of the disclosure on blocking PD-1-PD-L1 interaction were tested in a Jurkat-NFAT-PD-1 report gene assay.

A Chinese hamster ovary epithelial CHO-K1 cell line (ATCC, Cat #CCL-61) was maintained in F-12K medium containing 10% FBS in a humidified incubator with 5% CO2 at 37° C. Vectors comprising human PD-L1 encoding nucleic acid molecules (amino acid of NP_054862.1 as set forth in SEQ ID NO: 17) and vectors comprising OKT3-scFv encoding nucleic acid molecules (amino acid sequence set forth in SEQ ID NO: 18) were co-transfected to CHO-K1 cells using Polyethylenimine (MW25 kDa, Polyscience, Cat #23966-2), and a CHO-OKT3-PD-L1 cell line clone stably expressing human PD-L1 and OKT3-scFv was obtained by limited dilution.

A Jurkat-NFAT-PD-1 cell line was prepared by co-transfecting a Jurkat cell line (Cell Bank of the Chinese Academy of Sciences (Shanghai, China), Clone E6-1) with vectors comprising nucleic acid molecules encoding human PD-1 of SEQ ID NO: 19 and pGL4.30[luc2P/NFAT-RE/Hygro] (Promega. Cat #E848A) by electroporation, and a clone stably expressing human PD-1 and NFAT was obtained by limited dilution.

Figure 5:
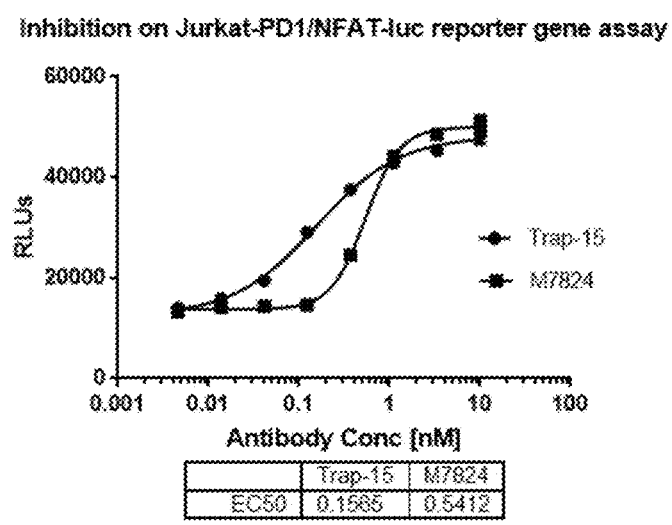
FIG. 5 shows the blocking activity of Trap-15 on PD-L1-PD-1 interaction.

Serially diluted Trap-15 and M7824 in RPMI 1640 Medium (Gibco, Cat #22400089) containing 1% FBS were plated on the 96-well plate (Corning, Cat #3917), 60 µl/well. The plate was then added with 60 µl/well cell suspension containing 30000 Jurkat-NFAT-PD1 cells and 20000 CHO-OKT3-PD-L1 cells in RPMI 1640 Medium with 1% FBS, and incubated in a 37° C., 5% $CO_2$ incubator for 16-18 hours. Then, 60 µl/well of One-Glo™ Reagent (Promega, Cat #E6130) was added to the assay plate, and luminescence was measured using a luminescence plate reader (Tecan, F200). The $EC_{50}$ values were calculated, and the dose-dependent curve was shown in FIG. 5.

The data suggested that Trap-15 had a better blocking activity on PD-1-PD-L1 interaction than M7824.

Example 8. Trap-15 Antagonize Human TGFβ1, Reinvigorated the PBMC Function

A cell based assay is performed to determine whether Trap-15 could reinvigorate human PBMC function in the presence of immune suppressor TGFβ 1.

Human PBMC was obtained from healthy donors. PBMC were isolated in SepMate-50 tubes (StemCell Technologies) containing Lymphoprep density gradient reagent (StemCell Technologies). 96-well plates (Corning, Cat #3799) were coated with 0.5 µg/mL functional-grade anti-CD3 (eBioscience, Cat #16-0037-85) in PBS at 4° C. overnight. On the next day, the coated plates were washed twice with DPBS buffer (Hyclone, Cat #SH30256.01). $1×10^5$/well PBMC were added to the plates. Serial diluted Trap-15, M7824, anti-PD-1 antibody (antibody 21F12-1F6) and IgG control negative control IgG (heavy chain: SEQ ID NO:22; light chain: SEQ ID NO:23) were mixed with human TGFβ1 (SinoBiological, Cat #10804-HNAC) separately and added to the plate, the final concentration of TGFβ1 in plate is 5 ng/mL. After cell culture at 37° C. for 72 h, supernatants were collected and tested for IFNγ levels with ELISA kit (R&D Systems, Cat #DY285B). Results were shown in FIG. 6.

The results indicated that Trap-15 could block both PD-1 and TGFβ1, reinvigorated the PBMCs, elevated the IFNγ levels in a dose dependent manner. Surprisingly, M7824 did not show any effect in this assay system.

Example 9. Trap-15 Did not Induce Antibody-Dependent Cell-Mediated Cytotoxicy (ADCC)

Fc region of Trap-15 is mutated to abolish ADCC effect. Antibody-Dependent Cell-Mediated Cytotoxicity (ADCC) assay was performed on CHO-K1/PD-1 expressing PD-1 to see whether Trap-15 has ADCC effect. The CHO-K1/PD-1 cells expressing PD-1 were prepared by transfecting vectors comprising nucleic acid sequence encoding human PD-1 (SEQ ID NO: 19) into the CHO-K1 cell line. A clone stably expressing human PD-1 was obtained by limited dilution.

CHO-K1PD-1 cells expressing PD-1 were seed at a density of 10,000 cells per well and were pre-incubated with 100 nM or 10 nM Trap-15 or IgG4 Control (heavy chain: SEQ ID NO:24; light chain: SEQ ID NO:25) in assay buffer (Phenol red free MEM medium (Gibco, Cat #41061-029)+ 1% FBS) for 30 min. PBMC effector cells from healthy donors were added to initiate the ADCC effects at E/T (effector cells PBMC/target cells CHO-K1/PD-1) ratios of 10:1, 25:1 or 50:1. The ADCC effect of the Rituximab on Raji cells was used as an internal control to assure the assay quality. After incubation in a 37° C., 5% $CO_2$ incubator for 24 hours, cell supernatants were collected and detected using Viability/Cytotoxicity Multiplex Assay Kit (Dojindo, Cat #CK17). Absorbance at $OD_{490nm}$ was read on F50 (Tecan). The percentages of cell lysis were calculated according the formula below % Cell lysis=100×($OD_{sample}$−$OD_{target\ cells\ plus\ effector\ cells}$)/($OD_{maximum\ release}$−$OD_{Minimum\ release}$).

Data was analyzed by Graphpad Prism.

The data showed in FIG. 7. indicated that Trap-15 did not induce ADCC effect on CHO-K1/PD-1 target cells.

Example 10. Trap-15 Did not Induce Complement-Dependent Cytotoxicity (CDC)

Fc region of Trap-15 is mutated to abolish CDC effect. Complement-Dependent Cytotoxicity (CDC) assay was performed on CHO-K1/PD-1 cells expressing PD-1 to see whether Trap-15 has CDC effect. CHO-K/PD-1 cells expressing PD-1 were seed at a density of 5,000 cells per well, incubated with serial diluted Trap-15 and IgG Control (heavy chain: SEQ ID NO:22; light chain: SEQ ID NO:23), (started from 50 μg/mL with 5 folds diluted to 7 concentration points) in assay buffer (Phenol red free MEM medium+ 1% FBS) for 30 min. The plates were then added with plasma from healthy donors at the final concentration 20 v/v % to initiate the CDC effects. After incubation in a 37° C., 5% $CO_2$ incubator for 4 hours, cells were added with Cell Counting-Lite 2.0 Luminescent Cell Viability Assay (Vazyme) and the RLU data was read on F200 (Tecan). The percentages of cell lysis were calculated according the formula below, % Cell lysis=100−(1−($RLU_{sample}$−$RLU_{Background}$)/($RLU_{cell+normal\ human\ plasma}$−$RLU_{Background}$)).

The data showed in FIG. 8 indicated that Trap-15 did not induce CDC effect on CHO-K1/PD-1 expressing PD-1 target cells.

Example 11. Anti-Tumor Effect of Trap-15 on MC38-OVA Model

The in vivo efficacy of Trap-15 was studied in hPD-1 knock-in mouse bearing MC38-OVA tumor model. For the experiment herein, human PD-1 extracellular portion knock-in mice C57BL/6J-Pdcd1$^{em1(PDCD1)Smoc}$ (Shanghai Model Organisms Center, Inc) were used.

MC38 cells were transduced with nucleic acid encoding ovalbumin (AAB59956) using retroviral transduction. The cells were subsequently cloned by limiting dilution. The clones highly expressing OVA protein were selected as MC38-OVA cell line.

C57BL/6J-Pdcd1$^{em1(PDCD1)Smoc}$ mice of 5-6 weeks were subcutaneously implanted with 1×10$^6$ MC38-OVA cells respectively, and were randomized into groups on Day 0 when the mean tumor volumes reached approximately 80 mm$^3$ (Length×Width$^2$/2). On Day 0, 3, 7, 10, 14 and 17, mice were intraperitoneally administered with 10 mg/kg Trap-15, Nivolumab (heavy chain: SEQ ID NO:20; light chain: SEQ ID NO:21) and PBS, respectively. Tumor volumes were monitored by caliper measurement twice per week during the study. Data is shown in Table 2 and FIG. 9 below.

Treatment with Trap-15 as monotherapy resulted in significant tumor growth inhibition compared to PBS group. Inhibition effect of Trap-15 is super over Nivolumab.

TABLE 2

MC38-OVA tumor growth inhibition

| Group | Dose | Animal number | Tumor volume(mm$^3$)$^a$ (on Day 21) | TGI (%)$^b$ | P$^c$ |
|---|---|---|---|---|---|
| PBS | / | 7 | 2137.8 ± 217.7 | / | / |
| Nivolumab | 10 mg/kg | 7 | 371.3 ± 205.4 | 82.13 | <0.001 |
| Trap-15 | 10 mg/kg | 6 | 174.5 ± 112.2 | 92.09 | <0.001 |

$^a$Tumor volume data were presented as Mean ± SEM;

$^b$ TGI = (1 − relative tumor volume in treated group/relative tumor volume in PBS group) *100%

$^c$ Compared to PBS group, two-way ANOVA were performed, followed by Tukey's multiple comparison test.

Example 12. Thermo Stabilities of Exemplary Fusion Proteins

The thermo stabilities of Trap-13, Trap-14 and Trap-15 were tested in this Example. Briefly, fusion proteins were stored at 40° C. for 2 week and subject to test on day 0, day 7 and day 14. Protein purity was measured by Size Exclusion Chromatography. In particular, 20 μg of a fusion protein was injected into a TSK G3000SWXL column, using 100 mM sodium phosphate+100 mM Na$_2$SO$_4$, pH 7.0, as running buffer. All measurements were performed on Agilent 1220 HPLC. Data was analyzed using OpenLAB software and summarized in Table 3.

The results indicated that Trap-13, Trap-14 and Trap-15 were relatively stable during the 2 week storage at a high temperature.

TABLE 3

Thermo stability of fusion proteins

| Fusion protein | Day | Aggregates (%) | Monomer (%) | Fragment (%) |
|---|---|---|---|---|
| Trap-13 | 0 | 2.57 | 97.43 | / |
|  | 7 | 3.00 | 96.88 | 0.11 |
|  | 14 | 5.09 | 94.38 | 0.53 |
| Trap-14 | 0 | 2.02 | 97.98 | / |
|  | 7 | 3.91 | 95.70 | 0.39 |
|  | 14 | 7.60 | 91.76 | 0.64 |
| Trap-15 | 0 | 0.69 | 99.31 | / |
|  | 7 | 2.17 | 97.68 | 0.14 |
|  | 14 | 6.07 | 93.63 | 0.30 |

The sequences in the present disclosure will be summarized below.

| Description/Sequence/SEQ ID NO |
| --- |

TGFβRII extracellular domain
IPPHVQKSVNNDMIVTDNNGAVKFPQLCKFCDVRFSTCDNQKSCMSNCSITSICEKPQEVCVAV
WRKNDENITLETVCHDPKLPYHDFILEDAASPKCIMKEKKKPGETFFMCSCSSDECNDNIIFSEE
YNTSNPD(SEQ ID NO: 1)

Anti-PD-1 antibody
Heavy chain variable region, in which CDR are determined according to Kabat (Kabat et al., Sequences
of Proteins of immunological interest, 5th Ed. Public Health Service, National Institutes of Health,
Bethesda, MD (1991))
QMQLVQSGAEVKKPGASVKLSCKASGYPFQSYYIHWVRQAPGQGLEWVG**VINPSGGSTTYA
QKFQGRVTMTRDTSISTAYMELSRLRSDDTVVYYCARGSYSSGWDYYVYYGMDV**WGKGTL
VTVSS(SEQ ID NO: 2)

Light chain variable region, in which CDR are determined according to Kabat (Kabat et al., Sequences
of Proteins of Immunological Interest, 5th Ed. Public Health Service, National Institutes of Health,
Bethesda, MD (1991))
DVVMTQSPLSITVITGEPASISCRSSQSLLHSQGYNYLDWYLQKPGQSPQLLIYLGSNRASGV
PDRFSGSGSGTDFTLKISRVEAEDVGVYYCMQALQTPWTGQGTKVEIK(SEQ ID NO: 3)

Heavy chain, in which the C-terminal amino acid K is replaced with A to fuse linker
QMQLVQSGAEVKKPGASVKLSCKASGYPFQSYYIHWVRQAPGQGLEWVGVINPSGGSTTYAQ
KFQGRVFMTRDTSISTAYMELSRLRSDDTVVYYCARGSYSSGWDYYYYGMDVWGKGTLVT
VSSASTKGPSVFPLAPSSKSTSGGTAALGCLVKDYEPEPVTVSWNSGALTSGVHTFPAVLQSSG
LYSLSSVVTVPSSSLGTQTYICNVNHKPSNTKVDKKVEPKSCDKTHTCPPCPAPEAAGGPSVFLF
PPKPKDTLMISRTPEVTCVVVAVSHEDPEVKFNWYVDGVEVHNAKTKPREEQYNSTYRVVSV
LTVLHQDWLNGKEYKCKVSNKALAAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHEA
LHNHYTQKSLSLSPGA(SEQ ID NO: 4)

Light chain
DVVMTQSPLSLPVTPGEPASISCRSSQSLLHSQGYNYLDWYLQKPGQSPQLLIYLGSNRASGVP
DRFSGSGSGTDFTLKISRVEAEDVGVYYCMQALQTPWTFGQGTKVEIKRTVAAPSVFIFPPSDE
QLKSGTASVVCLLNNFYPREAKVQWKVDNALQSGNSQESVTEQDSKDSTYSLSSTLTLSKADY
EKHKVYACEVTHQGLSSPVTKSFNRGEC (SEQ ID NO: 5)

Linker
SPAPELLGGPS(SEQ ID NO: 6)

DKTHTCPPCPAPELLGGPS(SEQ ID NO: 7)

SKYGPPCPPCGGPS(SEQ ID NO: 8)

GGGGSGGGGSGGGGSGGGGS(SEQ ID NO: 9)

Heavy chain-linker-TGFβRII extracellular domain
QMQLVQSGAEVKKPGASVKLSCKASGYPFQSYYIHWVRQAPGQGLEWVGVINPSGGSTITYAQ
KFQGRVTMTRDTSISTAYMELSRLRSDDTVVYYCARGSYSSGWDYYYYGMDVWGKGTLVT
VSSASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAAGGPSVFLF
PPKPKDTLMISRTPEVTCVVVAVSHEDPEVKFNWYVDGVEVHNAKTKPREEQYNSTYRVVSV
LTVLHQDWLNGKEYKCKVSNKALAAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHEA
LHNHYTQKSLSLSPGASPAPELLGGPSIPPHVQKSVNNDMIVTDNNGAVKFPQLCKFCDVRFST
CDNQKSCMSNCSITSICEKPQEVCVAVWRKNDENITLETVCHDPKLPYHDFILEDAASPKCIMK
EKKKPGETFFMCSCSSDECNDNIIFSEEYNTSNPD(SEQ ID NO: 10)

QMQLVQSGAEVKKPGASVKLSCKASGYPFQSYYIHWVRQAPGQGLEWVGVINPSGGSTTYAQ
KFQGRVTMTRDTSISTAYMELSRLRSDDTVVYYCARGSYSSGWDYYYYGMDVWGKGTLVT
VSSASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAAGGPSVFLF
PPKPKDTLMISRTPEVTCVVVAVSHEDPEVKFNWYVDGVEVHNAKTKPREEQYNSTYRVVSV
LTVLHQDWLNGKEYKCKVSNKALAAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHEA
LHNHYTQKSLSLSPGADKTHTCPPCPAPELLGGPSIPPHVQKSVNNDMIVTDNNGAVKFPQLCK
FCDVRFSTCDNQKSCNSNCSITSICEKPQEVCVAVWRKNDENITLETVCHDPKLPYHDFILEDA
ASPKCIMKEKKKPGETFFMCSCSSDECNDNIIFSEEYNTSNPD(SEQ ID NO: 11)

QMQLVQSGAEVKKPGASVKLSCKASGYPFQSYYIHWVRQAPGQGLEWVGVINPSGGSTTYAQ
KFQGRVTMTRDTSISTAYMELSRLRSDDTVVYYCARGSYSSGWDYYYYGMDVWGKGTLVT
VSSASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPEAAGGPSCFLF
PPKPKDTLMISRTPEVTCVVVAVSHEDPEVKFNWYVDGVEVHNAKTKPREEQYNSTYRVVSV
LTVLHQDWLNGKEYKCKVSNKALAAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHEA
LHNHYTQKSLSLSPGASKYGPPCPPCGGPSIPPHVQKSVNNDMIVTDNNGAVKFPQLCKFCDVR
FSTCDNQKSCMSNCSITSICEKPQEVCVAVWRKNDENITLETVCHDPKLPYHDFILEDAASPKCI
MKEKKKPGETFFMCSCSSDECNDNIIFSEEYNTSNPD(SEQ ID NO: 12)

| Description/Sequence/SEQ ID NO |
|---|
| QMQLVQSGAEVKKPGASVKLSCKASGYPFQSYYIHWVRQAPGQGLEWVGVINPSGGSTTYAQ<br>KFQGRVTMTRDTSISTAYMELSRLRSDDTVVYYCARGSYSSGWDYYYYGMDVWGKGTLVT<br>VSSASTKGPSVFPLAPSSKSTSGGTAALGCLVKDYFPEPVTVSWNSGALTSGVHTFPAVLQSSG<br>LYSLSSVVTVPSSSLGTQTYICNVNHKPSNTKVDKKVEPKSCDKTHTCPPCPAPEAAGGPSVFLF<br>PPKPKDTLMISRTPEVTCVVVAVSHEDPEVKFNWYVDGNTEVHNAKTKPREEQYNSTYRVVSV<br>LTVLHQDWLNGKEYKCKVSNKALAAPIEKTISKAKGQPREPQVYTLTPSRDELTKNQVSLTCL<br>VKGFYPSDTAVEWESNGQPENNYKTTPPVLEDSDGSFFLYSKLTVDKSRWQQGNVFSCSVMHEA<br>LHNHYTQKSLSLSPGAGGGGSGGGGSGGGGSGGGGSIPPHVQKSVNNDMIVTDNNGAVKFPQ<br>LCKFCDVRFSTCDNQKSCMSNCSITSICEKPQEVCVAVWRKNDENITLETVCHDPKLPYHDFIL<br>EDAASPKCIMKEKKKPGETFFMCSCSSDECNDNIIFSEEYNTSNPD(SEQ ID NO: 13) |

Positive control- anti-PD-1 antibody 21F12-1F6
Heavy chain
QMQLVQSGAEVKKPGASVKLSCKASGYIFQSYYIHWVRQAPGQGLEWVGVINPSGGSTT
YAQKFQGRVTMTRDTSISTAYMELSRLRSDDTVVYYCARGSYSSGWDYYYYGMDVWG
KGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPKSCDKTHTCPPCPAPE
AAGGPSVFLFPPKPKDTLMISRTPEVTCVVVAVSHEDPEVKFNWYVDGVEVHNAKTKPREEQY
NSTYRVVSVLTVLHQDWLNGKEYKCKVSNKALAAPIEKTISKAKGQPREPQVYTLPPSRDELT
KNQVSLTCLVKGFYPSDIAVEWESNGQPENNYKTTPPVLDSDGSFFLYSKLTVDKSRWQQGN
VFSCSVMHEALHNHYTQKSLSLSPGK(SEQ ID NO: 14)

Light chain (SEQ ID NO: 5)

Anti-PD-L1 antibody M7824
Heavy chain
EVQLLESGGGLVQPGGSLRLSCAASGFTFSSYIMMWVRQAPGKGLEWVSSIYPSGGITFYADTV
KGRFTISRDNSKNTLYLQMNSLRAEDTAVYYCARIKLGTVTTVSSASTKGPS
VFPLAPSSKSTSGGTAALGCLVKDYFPEPVTVSWNSGALTSGVHTFPAVLQSSGLYSLSSVVTV
PSSSLGTQTYIGNVNHKPSNTKVDKRVEPKSCDKTHTCPPCPAPELLGGPSVFLFPPKPKDTLMI
SRTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKS
LSLSPGAGGGGSGGGGSGGGGSGGGGSGIPPHVQKSVNNDMIVTDNNGAVKFPQLCKFCDVR
FSTCDNQKSCMSNCSITSICEKPQEVCVAVWRKNDENITLETVCHDPKLPYHDFILEDAASPKCI
MKEKKKPGETFFMCSCSSDECNDNIIFSEEYNTSNPD (SEQ ID NO: 15)

Light chain
QSALTQPASVSGSPGQSITISCTGTSSDVGGYNYVSWYQQHPGKAPKLMIYDVSNRPSGVSNRF
SGSKSGNTASLTISGLQAEDEADYYCSSYTSSSTRVFGTGTKVTVLGQPKANPTVTLFPPSSEEL
QANKATLVCLISDFYPGAVTVAWKADGSPVKAGVETTKPSKQSNNKYAASSYLSLTPEQWKS
HRSYSCQVTHEGSTVEKTVAPTECS (SEQ ID NO: 16)

Human PD-L1
MRIFAVFIFMTYWHLLNAFTVTVPKDLYVVEYGSNMTIECKFPVEKQLDLAALIVYWEMEDK
NIIQFVHGEEDLKVQHSSYRQRARLLKDQLSLGNAALQITDVKLQDAGVYRCMISYGGADYKR
ITVKVNAPYNKINQRILVVDPVTSEHELTCQAEGYPKAEVIWTSSDHQVLSGKTTTTNSKREEK
LFNVTSTLRINTTTNEIFYCTFRRLDPEENHTAELVIPELPLAHPPNERTHLVILGAILLCLGVALT
FIFRLRKGRMMDVKKCGIQDTNSKKQSDTHLEET (SEQ ID NO: 17)

OKT3-scFv
MERHWIFLLLLSVTAGVHSQVQLQQSGAELARPGASVKMSCKASGYTFTRYTMHWVKQRPG
QGLEWIGYINPSRGYTNYNQKFKDKATLTTDKSSSTAYMQLSSLTSEDSAVYYCARYYDDHYC
LDYWGQGTTLTVSSGGGGSGGGGSGGGGSQIVLTQSPAIMSASPGEKVTMTCSASSSVSYMN
WYQQKSGTSPKRWIYDTSKLASGVPAHFRGSGSGTSYSLTISGMEAEDAATYYCQQWSSNPFT
FGSGTKLEINSSVVPVLQKVNSTTTKPVLRTPSPVHPTGTSQPQRPEDCRPRGSVKGTGLDFACD
IYIWAPLAGICVALLLSLIITLICYRRSRKRVCKCPRPLVRQEGKPRPSEKIV (SEQ ID NO: 18)

Human PD-1
MQIPQAPWPVVWAVLQLGWRPGWFLDSPDRPWNPPTFSPALLVVTEGDNATFTCSFSNTSESF
VLNWYRMSPSNQTDKLAAFPEDRSQPGQDCRFRVTQLPNGRDFHMSVVRARRNDSGTYLCGA
ISLAPKAQIKESLRAELRVTERRAEVPTAHPSPSPRPAGQFQTLVVGVVGGLLGSLVLLVWVLA
VICSRAARGTIGARRTGQPLKEDPSAVPVFSVDYGELDFQWREKTPEPPVPCVPEQTEYATIVFP
SGMGTSSPARRGSADGPRSAQPLRPEDGHCSWPL (SEQ ID NO: 19)

Heavy chain for Nivolumab
QVQLVESGGGVVQPGRSLRLDCKASGITFSNSGMHWVRQAPGKGLEWVAVIWYDGSKRYYA
DSVKGRFTISRDNSKNTLFLQMNSLRAEDTAVYYCATNDDYWGQGTLVTVSSASTKGPSVFPL
APCSRSTSESTAALGCLVKDYFPEPVTVSWNSGALTSGVHTFPAVLQSSGLYSLSSVVTVPSSSL
GTKTYTCNVDHKPSNTKVDKRVESKYGPPCPPCPAPEFLGGPSVFLFPPKPKDTLMISRTPEVTC
VVVDVSQEDPEVQFNWYVDGVEVHNAKTKPREEQFNSTYRVVSVLTVLHQDWLNGKEYKCK
VSNKGLPSSIEKTISKAKGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNHYTQKSLSLSLGK
(SEQ ID NO: 20)

| Description/Sequence/SEQ ID NO |
|---|
| Light chain for Nivolurnab<br>EIVLTQSPATLSLSPGERATLSCRASQSVSSYLAWYQQKPGQAPRLLIYDASNRATGIPARFSGS<br>GSGTDFTLTISSLEPEDFAVYYCQQSSNWPRTFGQGTKVEIKRTVAAPSVFIFPPSDEQLKSGTAS<br>VVCLLNNFYPREAKVQWKVDNALQSGNSQESVTEQDSKDSTYSLSSTLTLSKADYEKHKVYA<br>CEVTHQGLSSPVTKSFNRGEC (SEQ ID NO: 21)<br><br>Heavy chain of IgG Control<br>QVQLVESGGGAVQPGRSLRLSCAASGFTFSSYGMHWVRQAPGKGLEWVAVILYDGSDKF<br>YADSVKGRFTISRDNSKNTLYLQMNSLRAEDTAVYYCAKVAVAGTHFDYWGQGTLVTVS<br>SASTKGPSVFPLAPCSRSTSESTAALGCLVKDYFPEPVTVSWNSGALTSGVHTFPAVLQSSG<br>LYSLSSVVTVPSSSLGTKTYTCNVDHKPSNTKVDKRVESKYGPPCPPCPAPEFLGGPSVFLF<br>PPKPKDTLMISRTPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPPSQEEMTKNQV<br>SLTCLVKGFYPSDIAVEWESNGQPENNYKTTPPVLDSDGSFFLYSRLTVDKSRWQEGNVFS<br>CSVMHEALHNHYTQKSLSLSLGK (SEQ ID NO: 22)<br><br>Light chain of IgG Control<br>DIQMTQSPSSISASVGDRVTITCRASQGIRNDLGWYQQKPGKAPKLLIYAASSLQSGVPSRFSGS<br>GSGTDFTLTISSLQPEDFATYYCQQLNSYPPTFGGGTKVEIKRTVAAPSVFIFPPSDEQLKSGTAS<br>VVCLLNNFYPREAKVQWKVDNALQSGNSQESVTEQSKDSTYSLSSTLTLSKADYEKHKVYA<br>CEVTHQGLSSPVTKSFNRGEC (SEQ ID NO: 23)<br><br>>IgG4 control heavy chain<br>QVQLVESGGGAVQPGRSLRLSCAASGFTFSSYGMHWVRQAPGKGLEWVAVILYDGSDKFYAD<br>SVKGRFTISRDNSKNTLYLQMNSLRAEDTAVYYCAKVAVAGTHFDYWGQGTLVTVSSASTKG<br>PSVFPLAPCSRSTSESTAALGCLVKDYFPEPVTVSWNSGALTSGVHTFPAVLQSSGLYSLSSVVT<br>VPSSSLGTKTYTCNVDHKPSNTKVDKRVESKYGPPCPPCPAPEFLGGPSVFLFPPKPKDTMISRL<br>TPEVTCVVVDVSQEDPEVQFNWYVDGVEVHNAKTKPREEQFNSTYRVVSVLTVLHQDWLNG<br>KEYKCKVSNKGLPSSIEKTISKAKGQPREPQVYTLPPSQEEMTKNQVSLTCLVKGFYPSDIAVE<br>WESNGQPENNYKTTPPVLDSDGSFFLYSRLTVDKSRWQEGNVFSCSVMHEALHNHYTQKSLSL<br>SLGK (SEQ ID NO: 24)<br><br>>IgG4 control Light chain<br>DIQMTQSPSSLSASVGDRVTITCRASQGIRNDLGWYQQKPGKAPKLLIYAASSLQSGVPSRFSGS<br>GSGTDFTLTISSLQPEDFATYYCQQLNSYPPTFGGGTKVEIKRTVAAPSVFIFPPSDEQLKSGTAS<br>VVCLLNNFYPREAKVQWKVDNALQSGNSQESVTEQDSKDSTYSLSSTLTLSKADYEKHKVYA<br>CEVTHQGLSSPVTKSFNRGEC (SEQ ID NO: 25) |

While the invention has been described above in connection with one or more embodiments, it should be understood that the invention is not limited to those embodiments, and the description is intended to cover all alternatives, modifications, and equivalents, as may be included within the spirit and scope of the appended claims. All referenced cited herein are further incorporated by reference in their entirety.

We claim:

1. A recombinant fusion protein, comprising
   a) human TGFβR2 extracellular domain, and
   b) an antibody or an antigen-binding fragment thereof binding to PD-1 and comprising 3 CDRs of a heavy chain variable region of SEQ ID NO: 2 and 3 CDRs of a light chain variable region of SEQ ID NO: 3,
   wherein the human TGFβR2 extracellular domain is linked to the C-terminus of the heavy chain of the antibody or the antigen-binding fragment thereof, and
   wherein the TGFβR2 extracellular domain comprises the amino acid sequence of SEQ ID NO: 1, or an amino acid sequence having at least 90% identity to SEQ ID NO: 1.

2. The recombinant fusion protein according to claim 1, wherein the antibody or the antigen-binding fragment thereof comprises a heavy chain variable region comprising the amino acid sequence of SEQ ID NO: 2 or an amino acid sequence having at least 90% identity to SEQ ID NO: 2 and simultaneously having the 3 CDRs of SEQ ID NO: 2, and a light chain variable region comprising the amino acid sequence of SEQ ID NO: 3 or an amino acid sequence having at least 90% identity to SEQ ID NO: 3 and simultaneously having the 3 CDRs of SEQ ID NO: 3.

3. The recombinant fusion protein according to claim 1, wherein the antibody or the antigen-binding fragment thereof comprises a heavy chain comprising the amino acid sequence of SEQ ID NO: 4 or an amino acid sequence having at least 80% identity to SEQ ID NO: 4 and simultaneously having the 3 CDRs of SEQ ID NO: 4, and a light chain comprising the amino acid sequence of SEQ ID NO: 5 or an amino acid sequence having at least 80% identity to SEQ ID NO:5 and simultaneously having the 3 CDRs of SEQ ID NO:5.

4. The recombinant fusion protein according to claim 1, wherein the TGFβR2 extracellular domain is linked via a linker to the C-terminus of the heavy chain (heavy chain-linker-TGFβR2 extracellular domain), or to the C-terminus of the heavy chain variable region (heavy chain variable region -linker-TGFβR2 extracellular domain).

5. The recombinant fusion protein according to claim 4, wherein the linker comprises an amino acid sequence of SEQ ID Nos.: 6, 7, 8 or 9.

6. The recombinant fusion protein according to claim 4, wherein the heavy chain-linker-TGFβR2 extracellular domain comprises an amino acid sequence selected from any one of SEQ ID Nos: 10, 11, 12 or 13 or an amino acid sequence having at least 80% identity to SEQ ID NOs: 10, 11, 12 or 13 respectively, and simultaneously having the 3 CDRs of corresponding SEQ ID NOs: 10, 11, 12 or 13 respectively.

7. The recombinant fusion protein according to claim 6, wherein the recombinant fusion protein comprises a light chain comprising the amino acid sequence of SEQ ID NO: 5 or an amino acid sequence having at least 80% identity to SEQ ID NO: 5 and simultaneously having the 3 CDRs of SEQ ID NO: 5.

8. The recombinant fusion protein according to claim 1, selected from:
   1) A recombinant fusion protein comprising the amino acid sequence of SEQ ID NO: 10 or an amino acid sequence having at least 80% identity to SEQ ID NO: 10 and simultaneously having the 3 CDRs of SEQ ID NO: 4; and the amino acid sequence of SEQ ID NO: 5 or an amino acid sequence having at least 80% identity to SEQ ID NO: 5 and simultaneously having the 3 CDRs of SEQ ID NO: 5;
   2) a recombinant fusion protein comprising the amino acid sequence of SEQ ID NO: 11 or an amino acid sequence having at least 80% identity to SEQ ID NO: 11 and simultaneously having the 3 CDRs of SEQ ID NO: 4, and the amino acid sequence of SEQ ID NO: 5 or an amino acid sequence having at least 80% identity to SEQ ID NO: 5 and simultaneously having the 3 CDRs of SEQ ID NO: 5;
   3) a recombinant fusion protein comprising the amino acid sequence of SEQ ID NO: 12 or an amino acid sequence having at least 80% identity to SEQ ID NO:12 and simultaneously having the 3 CDRs of SEQ ID NO: 4, and the amino acid sequence of SEQ ID NO: 5 or an amino acid sequence having at least 80% identity to SEQ ID NO: 5 and simultaneously having 3CDRs of SEQ ID NO: 5; or
   4) a recombinant fusion protein comprising the amino acid sequence of SEQ ID NO: 13 or an amino acid sequence having at least 80% identity to SEQ ID NO: 13 and simultaneously having the 3 CDRs of SEQ ID NO: 4, and the amino acid sequence of SEQ ID NO: 5 or an amino acid sequence having at least 80% identity to SEQ ID NO: 5 and simultaneously having 3CDRs of SEQ ID NO: 5.

9. A nucleic acid encoding the recombinant fusion protein according to claim 1.

10. A vector comprising the nucleic acid of claim 9.

11. A host cell comprising the nucleic acid of claim 9 or a vector comprising the nucleic acid of claim 9.

12. A method for producing a recombinant fusion protein, comprising a step of culturing the host cell of claim 11 under suitable conditions.

13. A recombinant fusion protein produced by the method of claim 12.

14. A pharmaceutical composition, comprising the recombinant fusion protein of claim 1, and at least one pharmaceutically acceptable carrier.

15. A method for treating colon cancer, comprising administering to a subject in need thereof a therapeutically effective amount of the recombinant fusion protein of claim 1, wherein the recombinant fusion protein comprises two polypeptides having the amino acid sequence of SEQ ID NO: 13 and two polypeptides having the amino acid sequence of SEQ ID NO: 5.

16. A pharmaceutical composition, comprising the recombinant fusion protein of claim 13, and at least one pharmaceutically acceptable carrier.

17. A method for treating colon cancer, comprising administering to a subject in need thereof a therapeutically effective amount of the pharmaceutical composition of claim 16, wherein the recombinant fusion protein comprised in the pharmaceutical composition comprises two polypeptides having the amino acid sequence of SEQ ID NO: 13 and two polypeptides having the amino acid sequence of SEQ ID NO: 5.

* * * * *